US010314965B2

(12) United States Patent
Holmer et al.

(10) Patent No.: US 10,314,965 B2
(45) Date of Patent: Jun. 11, 2019

(54) SEPARATION OF INTERFERENCE PULSES FROM PHYSIOLOGICAL PULSES IN A PRESSURE SIGNAL

(71) Applicant: GAMBRO LUNDIA AB, Lund (SE)

(72) Inventors: Mattias Holmer, Lund (SE); Bo Olde, Lund (SE); Kristian Solem, Kavlinge (SE); Leif Sornmo, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 307 days.

(21) Appl. No.: 14/917,099

(22) PCT Filed: Sep. 8, 2014

(86) PCT No.: PCT/EP2014/069098
§ 371 (c)(1),
(2) Date: Mar. 7, 2016

(87) PCT Pub. No.: WO2015/032948
PCT Pub. Date: Mar. 12, 2015

(65) Prior Publication Data
US 2016/0206804 A1 Jul. 21, 2016

(30) Foreign Application Priority Data
Sep. 9, 2013 (SE) ...................................... 1351040

(51) Int. Cl.
*A61M 1/00* (2006.01)
*A61M 1/36* (2006.01)
(Continued)

(52) U.S. Cl.
CPC ....... *A61M 1/3656* (2014.02); *A61B 5/02108* (2013.01); *A61B 5/7217* (2013.01);
(Continued)

(58) Field of Classification Search
None
See application file for complete search history.

(56) References Cited

U.S. PATENT DOCUMENTS 4,936,980 A * 6/1990 Harada ............... A61M 1/3496
210/321.65
5,004,459 A * 4/1991 Peabody ................ A61M 1/28
604/29
(Continued)

FOREIGN PATENT DOCUMENTS

CN 102686150 9/2012
CN 102834047 12/2012
(Continued)

OTHER PUBLICATIONS

Prosecution history of U.S. Appl. No. 13/001,314 (now U.S. Pat. No. 9,442,036) filed Dec. 23, 2010.
(Continued)

Primary Examiner — Evren Seven
(74) Attorney, Agent, or Firm — K&L Gates LLP

(57) ABSTRACT

A filtering device receives a signal from a pressure sensor in an extracorporeal fluid circuit connected to a subject and processes the signal to separate physiological pulses, e.g. from the subject's heart, from interference pulses, e.g. from a pump in the fluid circuit. The device repeatedly (iteratively) processes a signal segment by alternately subtracting (S3) a template signal from the signal segment, and applying a refinement processing (S6) to the resulting difference signal to generate a new template signal. By proper selection (S2) of the initial template signal, consecutive difference signals will alternately approximate the sequence of interference pulses in the signal segment and the sequence of physiological pulses in the signal segment. The refinement processing (S6) aims at alternately cleaning up unwanted residuals from interference pulses and physiological pulses, (Continued)

respectively, in the respective difference signal, so as to improve the accuracy of the template signal between the subtractions.

32 Claims, 12 Drawing Sheets

(51) Int. Cl.
    *A61B 5/00* (2006.01)
    *A61B 5/021* (2006.01)

(52) U.S. Cl.
    CPC .......... *A61B 5/7235* (2013.01); *A61B 5/4836* (2013.01); *A61M 2205/3331* (2013.01); *A61M 2230/30* (2013.01)

(56) References Cited

U.S. PATENT DOCUMENTS

| | | | |
|---|---|---|---|
| 5,580,460 A * | 12/1996 | Polaschegg | A61M 1/16 210/138 |
| 5,591,344 A * | 1/1997 | Kenley | A61L 2/04 210/636 |
| 5,624,551 A * | 4/1997 | Baumann | A61M 1/169 137/456 |
| 6,036,668 A * | 3/2000 | Mathis | A61M 1/28 604/29 |
| 6,526,357 B1 * | 2/2003 | Soussan | A61M 1/3496 702/100 |
| 2004/0034299 A1 | 2/2004 | Kandori et al. | |
| 2005/0010118 A1 | 1/2005 | Toyoda et al. | |
| 2010/0234786 A1 | 9/2010 | Fulkerson et al. | |
| 2011/0098582 A1 | 4/2011 | Takahashi et al. | |
| 2011/0106466 A1 | 5/2011 | Furmanski et al. | |
| 2011/0230772 A1 * | 9/2011 | Koball | A61B 5/0215 600/485 |
| 2013/0023776 A1 | 1/2013 | Olde et al. | |
| 2013/0053664 A1 | 2/2013 | Jian et al. | |
| 2013/0172803 A1 * | 7/2013 | Olde | A61B 5/0215 604/6.11 |
| 2013/0183209 A1 | 7/2013 | Richter et al. | |
| 2013/0299399 A1 | 11/2013 | Suffritti et al. | |
| 2014/0231319 A1 * | 8/2014 | Olde | A61B 5/02108 210/97 |
| 2015/0196742 A1 | 7/2015 | Browd et al. | |

FOREIGN PATENT DOCUMENTS

| | | |
|---|---|---|
| CN | 103002940 | 3/2013 |
| CN | 103200977 | 7/2013 |
| CN | 103249486 | 8/2013 |
| EP | 1769737 | 4/2007 |
| WO | 9710013 | 3/1997 |
| WO | 2003000777 | 1/2003 |
| WO | 2008007361 | 1/2008 |
| WO | 2009156174 | 12/2009 |
| WO | 2009156175 | 12/2009 |
| WO | 2010149726 | 12/2010 |
| WO | 2011080186 | 7/2011 |

OTHER PUBLICATIONS

Prosecution history of U.S. Appl. No. 13/380,631 (now U.S. Pat. No. 9,433,356) filed Mar. 16, 2012.
Prosecution history of U.S. Appl. No. 14/129,087 (now U.S. Pat. No. 9,427,513) filed Apr. 11, 2014.
Prosecution history of U.S. Appl. No. 12/988,146 (now U.S. Pat. No. 8,718,957) filed Oct. 15, 2010.
Prosecution history of U.S. Appl. No. 13/000,856 (now U.S. Pat. No. 8,715,216) filed Dec. 22, 2010.
Prosecution history of U.S. Appl. No. 14/270,246 (now U.S. Pat. No. 9,383,288) filed May 5, 2014.
Prosecution history of U.S. Appl. No. 13/519,532, filed Sep. 12, 2012.
Prosecution history of U.S. Appl. No. 14/123,397, filed Dec. 2, 2013.
Prosecution history of U.S. Appl. No. 13/519,483, filed Sep. 13, 2012.
Prosecution history of U.S. Appl. No. 13/519,559, filed Sep. 12, 2012.
Prosecution history of U.S. Appl. No. 14/234,527, filed May 5, 2014.
Prosecution history of U.S. Appl. No. 14/408,849, filed Dec. 17, 2014.
Prosecution history of U.S. Appl. No. 14/651,730, filed Jun. 12, 2015.
Prosecution history of U.S. Appl. No. 14/777,695, filed Sep. 16, 2015.
Prosecution history of U.S. Appl. No. 15/104,861, filed Jun. 15, 2016.
International Search Report for International Patent Application PCT/EP2014/069098 dated Dec. 1, 2014 (3 pages).
Written Opinion for International Patent Application PCT/EP2014/069098 dated Dec. 1, 2014 (6 pages).
M. Holmer, et al., "Determining Heart Activity Present in the Pressure Sensors of a Dialysis Machine," Computing in Cardiology, 2013; 40:217-220 (4 pages).

* cited by examiner

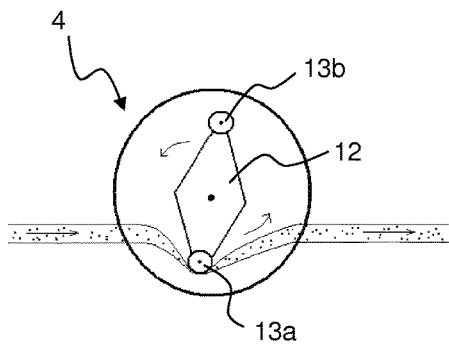
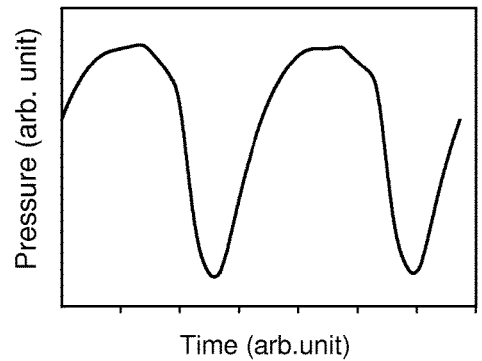
FIG. 3(a)       FIG. 3(b)
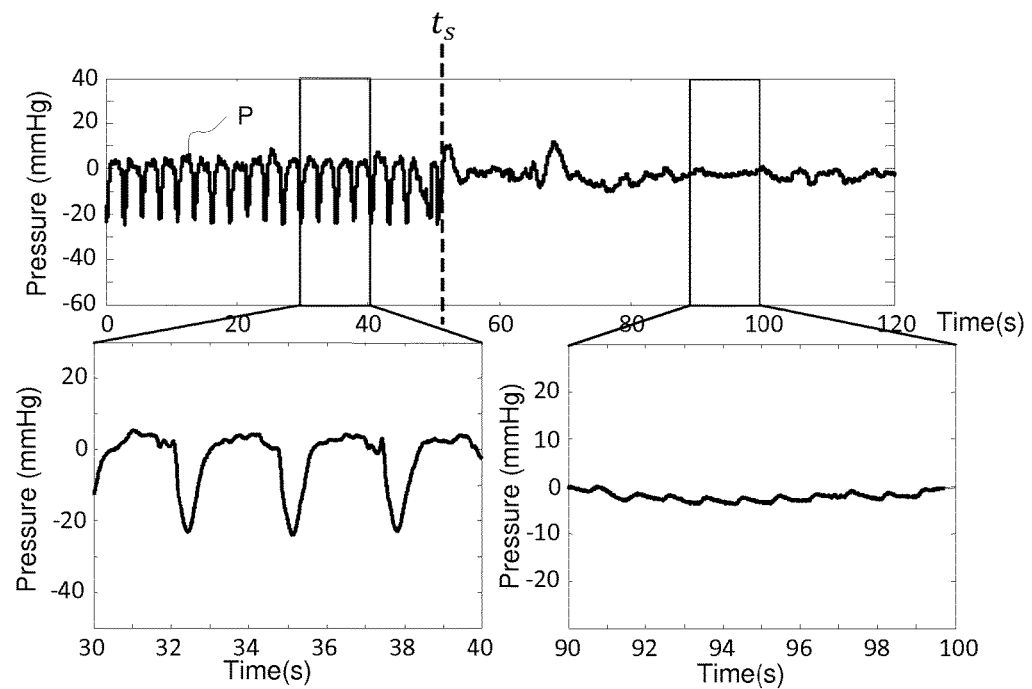
FIG. 4

SEPARATION OF INTERFERENCE PULSES FROM PHYSIOLOGICAL PULSES IN A PRESSURE SIGNAL

PRIORITY CLAIM

The present application is a National Phase of International Application No. PCT/EP2014/069098, filed on Sep. 8, 2014, which claims priority to Swedish Patent Application No. 1351040-9, filed Sep. 9, 2013, the entire contents of each of which is incorporated herein by reference and relied upon.

TECHNICAL FIELD

The present invention relates to a technique for processing a pressure signal obtained from a pressure sensor in an extracorporeal fluid circuit, in particular for the purpose of separating interference pulses from physiological pulses in the pressure signal. The interference pulses originate from an interference generator associated with the extracorporeal fluid circuit, and the physiological pulses originate from a physiological pulse generator in a subject connected to the extracorporeal fluid circuit. The present invention is e.g. applicable in connection with extracorporeal blood treatment.

BACKGROUND ART

In extracorporeal blood processing, blood is taken out of a human subject, processed (e.g. treated) and then reintroduced into the subject by means of an extracorporeal fluid circuit ("EC circuit") which is part of a blood processing apparatus. Generally, the blood is circulated through the EC circuit by a blood pump. In certain types of extracorporeal blood processing, the EC circuit includes an access device for blood withdrawal (e.g. an arterial needle or catheter) and an access device for blood reintroduction (e.g. a venous needle or catheter), which are inserted into a dedicated blood vessel access (e.g. fistula or graft) on the subject. Such extracorporeal blood treatments include hemodialysis, hemodiafiltration, hemofiltration, plasmapheresis, blood-banking, blood fraction separation (e.g. cells) of donor blood, apheresis, extracorporeal blood oxygenation, assisted blood circulation, extracorporeal liver support/dialysis, ultrafiltration, etc.

It is vital to minimize the risk for malfunctions in the EC circuit, since these may lead to a potentially life-threatening condition of the subject. Serious conditions may e.g. arise if the EC circuit is disrupted downstream of the blood pump, e.g. by a Venous Needle Dislodgement (VND) event, in which the venous needle comes loose from the blood vessel access. Such a disruption may cause the subject to be drained of blood within minutes. WO97/10013, US2005/0010118, WO2009/156174, WO2010/149726 and US2010/0234786 all propose various techniques for detecting a VND event by identifying an absence of heart or breathing pulses in a pressure signal from a pressure sensor ("venous pressure sensor") on the downstream side of the blood pump in the EC circuit.

Recently, it has also been shown to be possible to monitor and analyze the behavior of physiological pressure generators such as the heart or respiratory system, based on pressure recordings in the EC circuit. Various applications are found in WO2010/149726, WO2011/080189, WO2011/080190, WO2011/080191, WO2011/080194 which are incorporated herein by reference. For example, these applications include monitoring a subject's heart pulse rate, blood pressure, heart rhythm, cardiac output, blood flow rate through the blood vessel access ("access flow"), arterial stiffness, as well as identifying signs of stenosis formation within the blood vessel access, predicting rapid symptomatic blood pressure decrease and detecting, tracking and predicting various breathing disorders.

Furthermore, WO2011/080188 proposes a technique for identifying and signaling a reverse placement of the devices for blood withdrawal and blood reintroduction in the vascular access by detecting and analyzing physiological pulses in a pressure signal recorded in the EC circuit.

All of these monitoring techniques presume that the physiological pulses can be reliably detected in the pressure signal. To enable monitoring, it may be necessary to filter the pressure signal for removal or suppression of signal interferences. The signal interferences comprise pressure pulses ("pump pulses") originating from the blood pump, and may also comprise further interfering pressure pulses, e.g. caused by further pumps, valves, balancing chambers, etc in the EC circuit. It may be a challenging task to properly remove e.g. the pump pulses, since the rate of the physiological pulses and the rate of the blood pump, i.e. the blood flow through the EC circuit, may change over time. If the rate of physiological pulses matches the rate of pump pulses, it is not unlikely that the filtering will remove also the physiological pulses, causing the monitoring technique to fail. Filtering is also rendered difficult by the fact that the pump pulses generally are much stronger than the physiological pulses in the pressure signal.

The prior art comprises WO97/10013 which proposes a filtering technique denoted "notch-equivalent filter", which presumes that the frequency and phase of the blood pump are known. Sinus signals are generated at the known frequency and at multiples of the known frequency. The sinus signals are input to an adaptive filter, which adapts the amplitude and the phase of each sinus signal to the pressure signal to be filtered. The sinus signals are then subtracted from the pressure signal at the respective amplitude and phase.

The prior art also comprises WO2009/156175, which proposes that the pressure signal is filtered in the time-domain, by subtraction of a predicted signal profile of the pressure pulses originating from the blood pump. The predicted signal profile may be obtained by reference measurements or by simulations. In one implementation, the predicted signal profile is retrieved from a library of pre-stored reference profiles, based on the current operating frequency of the blood pump, and subtracted from the pressure signal, based on timing information given by a dedicated pump sensor or by a control signal for the blood pump. In another implementation, the predicted signal profile is retrieved and subtracted by a best match technique, in which the predicted signal profile is scaled and shifted so as to minimize differences to the pressure signal before the subtraction. In yet another implementation, the predicted signal profile and the pressure signal are input to an adaptive filter structure that operates to adapt its filter coefficients so as to produce an error signal in which the pressure pulses from the blood pump are suppressed.

WO2013/000777 proposes another filtering technique that may be implemented to suppress, in a pressure signal, first pulses that are known to occur in repeating pulse cycles in the pressure signal. Such first pulses may e.g. originate from a blood pump in an extracorporeal blood flow circuit. The proposed technique operates to filter the pressure signal by subtracting, for each current data sample in the pressure signal, a reference value which is calculated as a function of other data sample(s) in the same pressure signal. In one embodiment, the other data sample(s) are cycle-synchronized with the current data sample, which means that they have the same relative location in their respective pulse cycle as the current data sample in the current pulse cycle. Thereby, each reference value will represent an estimation of the instant signal contribution from first pulse(s) within the current pulse cycle. By subtracting this instant signal contribution from the respective current data sample, a time-sequence of output samples can be generated for the current pulse cycle so as to be essentially free of first pulses.

There is a continued need to achieve an improved filtering technique, in terms of one or more of the following: ability to handle changes in the rates of physiological pulses and interference pulses (e.g. pump pulses), ability to handle overlap in frequency and/or time between interference pulses and physiological pulses, complexity of the filtering technique, ability to generate the filtered signal in real time, processing efficiency and memory usage during filtering, accuracy of the filtered signal, and robustness of the filtering technique.

SUMMARY

It is an objective of the invention to at least partly overcome one or more limitations of the prior art.

Another objective is to provide a filtering technique capable of meeting one or more of the above-mentioned needs.

One or more of these objectives, as well as further objectives that may appear from the description below, are at least partly achieved by devices for filtering a pressure signal, methods of filtering a pressure signal and computer-readable media according to the independent claims, embodiments thereof being defined by the dependent claims.

Embodiments of the invention have been devised based on the insight that it is possible to separate two different type of pulses (denoted A pulses and B pulses in the following discussion) from each other in a signal segment by implementing a sequence of template subtractions, each followed by a signal refinement to remove unwanted residuals from the respective subtraction. First, an initial template signal is subtracted from the signal segment for the purpose of removing B pulses while retaining A pulses. Imperfections in the initial template signal cause the resulting "first difference signal" to contain unwanted residuals (remainders) of the B pulses. Then, the first difference signal is processed by signal refinement for the purpose of further suppressing these residuals. Thereby, the signal refinement results in an improved representation of the sequence of A pulses in the signal segment, i.e. a template signal for the A pulses. By subtracting the template signal for the A pulses from the signal segment, another difference signal ("second difference signal") is generated that represents the sequence of B pulses in the signal segment. Again, imperfections in the template signal for the A pulses cause the second difference signal to contain unwanted residuals, this time residuals of the A pulses. Therefore, the second difference signal is processed by signal refinement for the purpose of further suppressing these residuals. The signal refinement results in an improved representation of the sequence of B pulses in the signal segment, i.e. a template signal for the B pulses. It is realized that this process of alternate template subtraction and signal refinement results in a separation of the A and B pulses into the first and second difference signals, as well as into the respective template signal.

Embodiments of the invention have also been devised based on the insight that it is possible to further improve the representation of the respective pulses in the signal segment by subtracting the template signal for the B pulses from the signal segment to generate a new difference signal, which is an updated version of the first difference signal, and then repeat the steps of alternate signal refinement and template subtraction for a number of iterations. This iterative approach has the ability of significantly improving the accuracy of the difference signals and the template signals, and thereby generate accurate representations of the timing, shape and magnitude of the A and B pulses in the signal segment. It should be noted that the signal segment may contain further types of pulses, which thus also may be represented in the respective difference signal after each template subtraction.

It should also be noted that the above-described technique may be extended for separating more than two different types of pulses, e.g. A, B and C pulses. In an example of such a variant, two initial template signals (e.g. one for B pulses and one for C pulses), or a common initial template signal, may be subtracted from the signal segment for the purpose of removing B pulses and C pulses while retaining A pulses. The first difference signal will contain unwanted residuals of the B and C pulses. The first difference signal is processed by signal refinement, to generate a template signal for the A pulses. The template signal for the A pulses and the initial template signal for the B pulses are subtracted from the signal segment, to generate an intermediate difference signal that represents the C pulses in the signal segment. The intermediate difference signal will contain unwanted residuals of the A and B pulses. The intermediate difference signal is processed by signal refinement, to generate a template signal for the C pulses. The template signal for the C pulses and the template signal for the A pulses are subtracted from the signal segment, to generate a second difference signal that represents the B pulses in the signal segment. The second difference signal will contain unwanted residuals of the A and C pulses. The second difference signal is processed by signal refinement, to generate a template signal for the B pulses. By analogy with the foregoing example, the accuracy of the separated pulses may be improved by subtracting the template signals for the B and C pulses from the signal segment, so as to once again generate the first difference signal and by iterating over the above-described operations of signal refinement and template subtraction. The example of separating A, B and C pulses may be regarded to include a first subtraction of two initial template signals (for B and C pulses), a signal refinement of the resulting first difference signal for generation of the template signal for the A pulses, an intermediate step of generating the template signal for the C pulses (which incidentally also involves template subtraction and signal refinement), a second subtraction of the template signals for the A and C pulses, and a signal refinement of the resulting second difference signal for generation of the template signal for the B pulses.

Embodiments of the above-described technique are applied for separating pulses in a pressure signal, specifically interference pulses originating from an interference generator in an extracorporeal fluid circuit, and physiological pulses originating from a physiological pulse generator in a subject connected to the extracorporeal fluid circuit.

With reference to the foregoing examples, it is to be understood that the pressure signal may contain one or more additional types of pulses, which may or may not be separated as well. Such an additional type of pulses may e.g. originate from an additional physiological pulse generator in the subject, or an additional interference generator associated with the extracorporeal fluid circuit.

When applied for separating interference pulses and physiological pulses, the inventive technique may start by generating the first difference signal to represent either the physiological pulses or the interference pulses. These two main implementation variants of the overall inventive technique are defined separately as first to fourth aspects and fifth to eighth aspects, respectively, of the invention.

A first aspect of the invention is a device for processing a pressure signal obtained from a pressure sensor in an extracorporeal fluid circuit. The device comprising: an input for receiving the pressure signal from the pressure sensor; and a signal processor connected to the input and being configured to extract, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit. The signal processor is further configured to process the signal segment for separation of the interference pulses from the physiological pulses by:

a) subtracting at least one initial template signal from the signal segment to generate a first difference signal that represents the sequence of physiological pulses and residuals of the interference pulses;

b) processing the first difference signal to generate a first template signal in which the residuals of the interference pulses are suppressed in relation to the sequence of physiological pulses;

c) subtracting at least the first template signal from the signal segment to generate a second difference signal that represents the sequence of interference pulses and residuals of the physiological pulses; and d) processing the second difference signal to generate a second template signal in which the residuals of the physiological pulses are suppressed in relation to the sequence of interference pulses.

In one embodiment, the signal processor is configured to, subsequent to the steps a)-d), process the signal segment for separation of the interference pulses from the physiological pulses by: e) subtracting at least the second template signal from the signal segment to generate the first difference signal, and repeating the steps b)-e) in at least one iteration.

In one embodiment, the signal processor is configured to repeatedly execute steps b)-e) until a predefined convergence criterion is fulfilled or until a predefined time limit is exceeded. The predefined convergence criterion may be defined to detect a predefined suppression of the residuals of the physiological pulses in the second difference signal or the second template signal, or to detect a predefined suppression of the residuals of the interference pulses in the first difference signal or the first template signal. In an implementation, the predefined convergence criterion is configured to evaluate a correspondence in timing of physiological or interference pulses between consecutive iterations of steps b)-e), e.g. apparent physiological pulses within the first difference signal or within the first template signal, or apparent interference pulses within the second difference signal or within the second template signal. In another implementation, the predefined convergence criterion is configured to evaluate a correspondence in signal shape for at least one of the generated signals between consecutive iterations of steps b)-e). In another implementation, the predefined convergence criterion is configured to evaluate a correspondence in signal shape between signals generated during an iteration of steps b)-e), e.g. between the first difference signal and the first template signal, or between the second difference signal and the second template signal. In another implementation, the predefined convergence criterion is configured to evaluate a correspondence in signal shape between the signal segment and a superposition of the first and second difference signals or the first and second template signals.

In one embodiment, the signal processor is further configured, in step b), to: identify a set of predefined first cycles of the physiological pulses in the first difference signal, determine a first signal profile for each of the predefined first cycles, and generate the first template signal by tiling the first signal profiles such that the timing of the first signal profiles in the first template signal matches the timing of the set of predefined first cycles in the first difference signal.

The signal processor may be further configured, in step b), to: identify a respective reference time point for each of the predefined first cycles in the first difference signal, and generate the first template signal by tiling and time-scaling the first signal profiles with respect the reference time points.

The signal processor may be further configured, in step b), to: determine a length of the respective predefined first cycle in the first difference signal; and select the first signal profile among at least two candidate profiles based on the length of the respective predefined first cycle.

The signal processor may be further configured, in step b), to determine the first signal profile by at least one of: retrieving the first signal profile from an electronic memory associated with the device, wherein the first signal profile is fixed and pre-defined, or generated and stored in the electronic memory by the signal processor during processing of a preceding signal segment in the pressure signal; generating the first signal profile as a function of the predefined first cycles in the first difference signal; generating the first signal profile by processing the pressure signal while the interference generator is intermittently disabled; and generating the first signal profile by processing a further pressure signal acquired from a further pressure sensor in the extracorporeal fluid circuit.

In one embodiment, the signal processor is further configured, in step d), to: identify a set of predefined second cycles in the second difference signal; determine a second signal profile for each of the predefined second cycles; and generate the second template signal by tiling the second signal profiles such that the timing of the second signal profiles in the second template signal matches the timing of the set of predefined second cycles in the second difference signal.

The signal processor may be further configured, in step d), to: identify a respective reference time point for each of the predefined second cycles in the second difference signal, and generate the second template signal by tiling and time-scaling the second signal profiles with respect the reference time points.

The signal processor may be further configured, in step d), to determine the second signal profile by one of: retrieving the second signal profile from an electronic memory associated with the device, wherein the second signal profile is fixed and pre-defined, or generated and stored in the electronic memory by the signal processor during processing of a preceding signal segment in the pressure signal; retrieving the second signal profile from the electronic memory based on an operating condition of the extracorporeal fluid circuit, wherein a plurality of second signal profiles are stored in the electronic memory in association with different operating conditions; generating the second signal profile as a function of the predefined second cycles in the second difference signal; mapping the predefined second cycles in the second difference signal to corresponding subsets of the signal segment, and generating the second signal profile as a function of the corresponding subsets; and generating the second signal profile by processing a further pressure signal acquired from a further pressure sensor in the extracorporeal fluid circuit.

In an alternative embodiment, the signal processor is further configured, in step d), to: determine a current operating condition of the interference generator; and generate the second template signal as a combination of sinusoids at a plurality of harmonic frequencies associated with the current operating condition.

In one embodiment, the signal processor is further configured, in step a) to: acquire said at least one initial template signal as an initial estimate of the shape, the magnitude and the timing of the interference pulses in the signal segment.

In one embodiment, the signal processor is further configured, in step a), to acquire said at least one initial template signal by one of: determining a current operating condition of the interference generator, determining an initial signal profile for predefined second cycles in the signal segment, and generating said at least one initial template signal by tiling the initial signal profiles such that the timing of the initial signal profiles in said at least one initial template signal corresponds to the current operating condition; determining a current operating condition of the interference generator, and generating said at least one initial template signal as a combination of sinusoids at a plurality of harmonic frequencies associated with the current operating condition; and retrieving said at least one initial template signal from an electronic memory associated with the device, wherein said at least one initial template signal is generated and stored in the electronic memory by the signal processor during processing of a preceding signal segment in the pressure signal, preferably as a function of at least one of the second difference signal, the second template signal and the second signal profile generated during the processing of the preceding signal segment.

In the foregoing embodiments, the signal processor may be configured to determine the current operating condition of the interference generator, e.g. the current operating frequency, by processing one of the signal segment, the first difference signal, the second difference signal, or a reference signal that represents the operation of the interference generator.

In the foregoing embodiments, each predefined first cycle may be predefined to comprise a given number of physiological pulses, and preferably one and only one physiological pulse.

In the foregoing embodiments, each predefined second cycle may be predefined to comprise a given number of interference pulses.

In the foregoing embodiments, the interference generator may be a peristaltic pump comprising a rotor with at least one roller, and each predefined second cycle pulses may be predefined to correspond to a full revolution of the rotor.

In one embodiment, the signal processor is configured to extract the signal segment such that the signal segment comprises at least 2, and preferably at least 10 physiological pulses, and at least 2, and preferably at least 10, interference pulses.

A second aspect of the invention is a method of processing a pressure signal obtained from a pressure sensor in an extracorporeal fluid circuit. The method comprises: extracting, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit; a) subtracting at least one initial template signal from the signal segment to generate a first difference signal that represents the sequence of physiological pulses and residuals of the interference pulses; b) processing the first difference signal to generate a first template signal in which the residuals of the interference pulses are suppressed in relation to the sequence of physiological pulses; c) subtracting at least the first template signal from the signal segment to generate a second difference signal that represents the sequence of interference pulses and residuals of the physiological pulses; and d) processing the second difference signal to generate a second template signal in which the residuals of the physiological pulses are suppressed in relation to the sequence of interference pulses.

A third aspect of the invention is a computer-readable medium comprising computer instructions which, when executed by a processor, cause the processor to perform the method of the second aspect.

A fourth aspect of the invention is a device for processing a pressure signal obtained from a pressure sensor in an extracorporeal fluid circuit. The device comprises: segmentation means configured to receive the pressure signal and extract, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit; first subtraction means configured to subtract at least one initial template signal from the signal segment to generate a first difference signal that represents the sequence of physiological pulses and residuals of the interference pulses; first refinement means configured to process the first difference signal to generate a first template signal in which the residuals of the interference pulses are suppressed in relation to the sequence of physiological pulses; second subtraction means configured to subtract at least the first template signal from the signal segment to generate a second difference signal that represents the sequence of interference pulses and residuals of the physiological pulses; and second refinement means configured to process the second difference signal to generate a second template signal in which the residuals of the physiological pulses are suppressed in relation to the sequence of interference pulses.

Any one of the above-identified embodiments of the first aspect may be adapted and implemented as an embodiment of the second to fourth aspects.

A fifth aspect of the invention is a device for processing a pressure signal obtained from a pressure sensor in an extracorporeal fluid circuit. The device comprises: an input for receiving the pressure signal from the pressure sensor; and a signal processor connected to the input and being configured to extract, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit. The signal processor is further configured to process the signal segment for separation of the interference pulses from the physiological pulses by:

a) subtracting at least one initial template signal from the signal segment to generate a first difference signal that represents the sequence of interference pulses and residuals of the physiological pulses, b) processing the first difference signal to generate a first template signal in which the residuals of the physiological pulses are suppressed in relation the sequence of interference pulses, c) subtracting at least the first template signal from the signal segment to generate a second difference signal that represents the sequence of physiological pulses and residuals of the interference pulses, and d) processing the second difference signal to generate a second template signal in which the residuals of the interference pulses are suppressed in relation to the sequence of physiological pulses.

A sixth aspect of the invention is a method of processing a pressure signal obtained from a pressure sensor in an extracorporeal fluid circuit. The method comprises: extracting, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit; a) subtracting at least one initial template signal from the signal segment to generate a first difference signal that represents the sequence of interference pulses and residuals of the physiological pulses; b) processing the first difference signal to generate a first template signal in which the residuals of the physiological pulses are suppressed in relation the sequence of interference pulses; c) subtracting at least the first template signal from the signal segment to generate a second difference signal that represents the sequence of physiological pulses and residuals of the interference pulses; and d) processing the second difference signal to generate a second template signal in which the residuals of the interference pulses are suppressed in relation to the sequence of physiological pulses.

An seventh aspect of the invention is a computer-readable medium comprising computer instructions which, when executed by a processor, cause the processor to perform the method of the sixth aspect.

An eighth aspect of the invention is a device for processing a pressure signal obtained from a pressure sensor in an extracorporeal fluid circuit. The device comprises: segmentation means configured to receive the pressure signal and extract, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit; first subtraction means configured to subtract at least one initial template signal from the signal segment to generate a first difference signal that represents the sequence of interference pulses and residuals of the physiological pulses; first refinement means configured to process the first difference signal to generate a first template signal in which the residuals of the physiological pulses are suppressed in relation the sequence of interference pulses; second subtraction means configured to subtract at least the first template signal from the signal segment to generate a second difference signal that represents the sequence of physiological pulses and residuals of the interference pulses; and second refinement means configured to process the second difference signal to generate a second template signal in which the residuals of the interference pulses are suppressed in relation to the sequence of physiological pulses.

Any one of the above-identified embodiments of the first aspect may be adapted and implemented as an embodiment of the fifth to eighth aspects.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

FIG. 3(a) is a side view of a rotor of a peristaltic pump, and FIG. 3(b) is a plot of pressure pulses generated during a full rotation of the rotor in FIG. 3(a), as measured by a pressure sensor in the extracorporeal blood processing apparatus of FIG. 1.

FIG. 4 illustrates a pressure signal acquired during a time period when a blood pump is operating and then is stopped.

DETAILED DESCRIPTION OF EXAMPLE EMBODIMENTS

Figure 1:
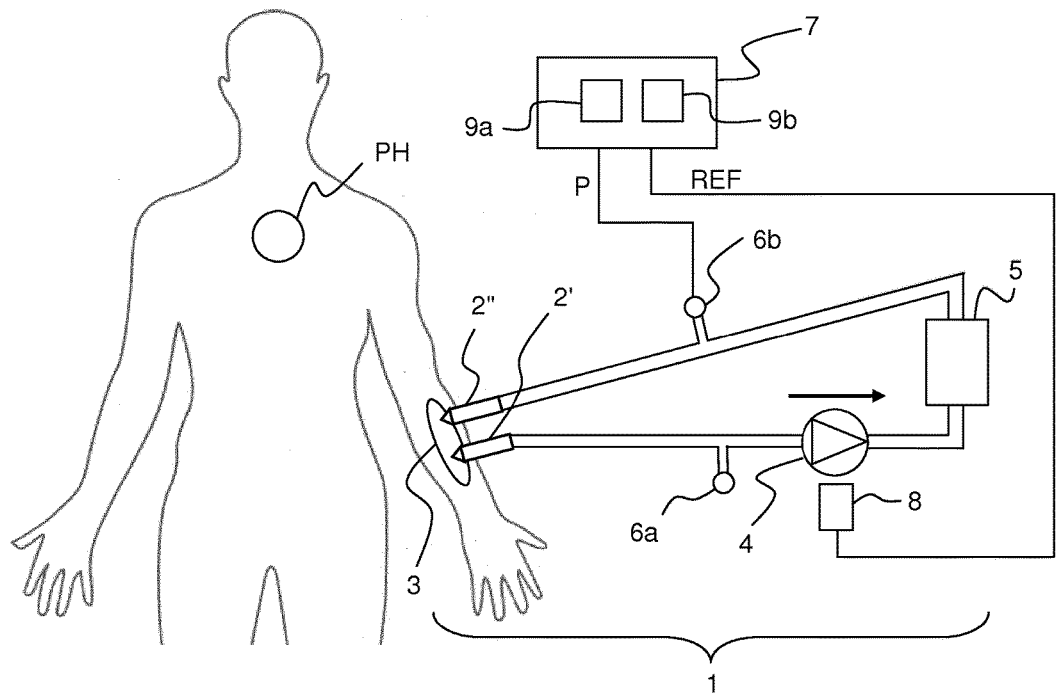
FIG. 1 a schematic diagram of a blood path in an extracorporeal blood processing apparatus attached to a human subject.

Throughout the description, the same reference numerals are used to identify corresponding elements.

FIG. 1 illustrates a human subject which is connected to an extracorporeal fluid circuit 1 by way of access devices 2', 2" inserted into a dedicated vascular access 3 (also known as "blood vessel access") on the subject. The extracorporeal fluid circuit 1 (denoted "EC circuit" in the following) is configured to transport blood to and from the cardiovascular system of the subject. In one example, the EC circuit 1 is part of an apparatus for blood processing, such as a dialysis machine. In the illustrated example, a blood pump 4 draws blood from the vascular access 3 via access device 2' and pumps the blood through a blood processing unit 5, e.g. a dialyzer, and back to the vascular access 3 via access device 2". Thus, when both access devices 2', 2" are connected to the vascular access 3, the EC circuit 1 defines a blood path that starts and ends at the vascular access 3. The EC circuit 1 may be seen to comprise a "venous side" which is the part of the blood path located downstream of the blood pump 4, and an "arterial side" which is the part of the blood path located upstream of the pump 4.

Pressure sensors 6a and 6b are arranged to detect pressure waves in the EC circuit 1. As used herein, a "pressure wave" is a mechanical wave in the form of a disturbance that travels or propagates through a material or substance. In the context of the following examples, the pressure waves propagate in the blood in the cardiovascular system of the subject and in the blood path of the EC circuit 1 at a velocity that typically lies in the range of about 3-20 m/s. The sensors 6a, 6b, which are in direct or indirect hydraulic contact with the blood, generates pressure data that forms a pressure pulse for each pressure wave. A "pressure pulse" is thus a set of signal values that define a local increase or decrease (depending on implementation) in signal magnitude within a time-dependent measurement signal ("pressure signal") P.

Figure 2:
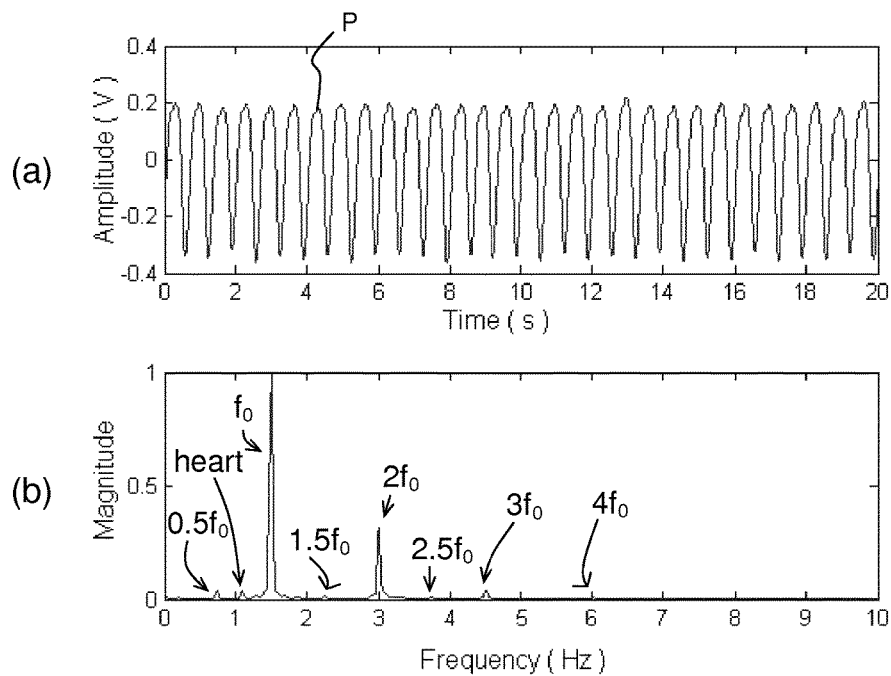
FIG. 2(a) is a plot in the time domain of a pressure signal containing both pump frequency components and a heart frequency component.
FIG. 2(b) is a plot of the corresponding signal in the frequency domain.

FIG. 2(a) shows an example of a time-resolved pressure signal P acquired from the venous pressure sensor 6b, and FIG. 2(b) shows the corresponding spectral density, i.e. signal energy as a function of frequency. The spectral density reveals that the pressure signal P contains frequency components that emanate from and are given by the design of the blood pump 4. As seen, the frequency components are a set of harmonic frequencies $0.5f_0$, $f_0$, $1.5f_0$, $2f_0$, etc. In the illustrated example, the blood pump 4 is a rotary peristaltic pump of the type depicted in FIG. 3(a), and the frequency components are governed by the revolution of the rotor 12 and the engagement of the rollers 13a, 13b with the tube segment. The dominating frequency $f_0$ is the pumping frequency, i.e. the frequency of pump strokes, with each pump stroke being generated by the engagement of one of the rollers 13a, 13b with the tube segment. FIG. 3(b) illustrates the pressure pulsations ("pump pulses") in the pressure signal that originate exclusively from the pump 4 during one revolution of the rotor 12. Thus, the pump pulses in FIG. 3(b) represent the pressure waves that are generated by the rollers 13a, 13b engaging the tube segment during a full rotor revolution. Returning to FIGS. 2(a)-2(b), the pressure signal P also includes pressure pulsations ("heart pulses") that originate from the beating of the heart in the patient. In this example, the heart pulses are much weaker than the pump pulses and are difficult to detect in the pressure signal P (FIG. 2(a)), which is dominated by the pump pulses. This is further illustrated in FIG. 4, which shows a pressure signal P acquired from the venous pressure sensor 6b before and after a time point $t_s$ at which the pump 4 is stopped. The bottom plots in FIG. 4 are enlarged views of the pressure signal when the pump 4 is operating and stopped, respectively. It is seen that heart pulses are visible in the pressure signal when the pump 4 is stopped, whereas the pressure signal is dominated by the pump pulses when the pump 4 is operating.

Generally, the pressure signal P may contain pressure pulses ("physiological pulses") from any physiological pulse generator PH (FIG. 1), periodic or non-periodic, in the patient, including reflexes, voluntary muscle contractions, non-voluntary muscle contractions, the heart, the breathing system, the autonomous system for blood pressure regulation and the autonomous system for body temperature regulation. However, for the purposes of the following examples, it is assumed that the pressure signal P contains only pump pulses and heart pulses.

Returning to the example of FIG. 1, a filtering device 7 is connected to the sensor 6b by a transmission line to acquire and process the pressure signal P, for the purpose of separating the pump pulses from the heart pulses and generating output data based on either the heart pulses or the pump pulses. Thus, the output data may represent the activity of the heart PH in the subject that is connected to the EC circuit 1. For example, the output data may be in the form of a filtered pressure signal ("heart signal"), in which the heart pulses are retained while the pump pulses have been eliminated or at least significantly suppressed. In another example, the output data may indicate the timing of individual heart pulses in the pressure signal P. In yet another example, the output data is an average shape of the heart pulses. In another alternative, the output data may be provided to indicate a dislodgement of the venous access device 2" from the vascular access 3. Alternatively, the output data may be provided as one or more values of a cardiovascular parameter, which is related to a property of either the heart or the blood vessels in the patient. For example, the cardiovascular parameter may represent one or more of the arterial status (arterial stiffness) of the blood vessels, the degree of calcification of the blood vessels, and the status of the blood vessel access. Another parameter may be calculated to indicate a reversed positioning of the access devices 2', 2" in the vascular access 3. In other embodiments, the cardiovascular parameter value may represent one of more of heart rate variability (HRV), the heart rate (HR), heart rate turbulence (HRT), rate of ectopic beats (ectopic beat count, EBC), or the origin of ectopic beats (e.g. atria/ventricular). In another alternative, the output data may be in the form of a filtered pressure signal ("pump signal"), in which the pump pulses are retained while the heart pulses have been eliminated or at least significantly suppressed. By the same token, the output data may represent a property of the pump 4, e.g. an average shape of the pump pulses, the timing of pump pulses, the operating frequency of the pump 4, or a condition parameter that indicates the condition of the pump 4, e.g. to signal a potential mechanical problem in the pump 4.

In the implementation shown in FIG. 1, the device 7 is connected to receive a reference signal REF which at least approximately indicates one of the harmonic frequencies of the pump 4. The reference signal REF may be used by the device 7 in the process of separating the pump pulses from the heart pulses. In FIG. 1, the reference signal REF is generated by a reference sensor 8 associated with the pump 4 to measure the rotation speed of an element (e.g. the rotor 12) in the power transmission of the pump 4. For example, the reference sensor 8 may be a tachometer which is configured to provide any number of readings representative of the rotation speed during each rotor revolution, e.g. at a single instance or at plural instances during each rotor revolution. For example, the tachometer may generate pulses in the reference signal REF to indicate the timing of one or more predefined rotor positions, e.g. by a Hall sensor or an optical sensor, as is well-known in the art. In another example, not shown, the reference signal REF is a control signal for the pump 4, e.g. indicating a set value for the blood flow rate or the pumping frequency of the pump 4, or indicating the current/power fed to a motor that drives the pump 4. In another example, not shown, the reference signal REF is a pressure signal generated by another pressure sensor in the EC circuit 1 (e.g. the sensor 6a) which is arranged to detect pressure waves originating from the pump 4. There are many techniques, well known to the skilled person, for determining the current operating frequency of the pump 4 from any one of these types of reference signals.

Although not shown herein, it is to be understood that the filtering device 7 may instead be connected to separate pump pulses from heart pulses in a pressure signal from sensor 6a, or in pressure signals from more than one pressure sensor in the EC circuit 1.

Depending on implementation, the device 7 may use digital components or analog components, or a combination thereof, for acquiring and processing the pressure signal. The device 7 may be a computer, or a similar data processing device, with adequate hardware for acquiring and processing the pressure signal in accordance with different embodiments of the invention. Embodiments of the invention may e.g. be implemented by software instructions that are supplied on a computer-readable medium for execution by a processor 9a in conjunction with an electronic memory 9b in the device 7. The computer-readable medium may be a tangible product (e.g. magnetic medium, optical disk, read-only memory, flash memory, etc) or a propagating signal.

The filtering device 7 is designed based on the insight that it is possible to separate heart pulses and pump pulses that are superimposed in a signal segment of the pressure signal P by repeatedly (iteratively) subtracting a template signal from the signal segment to generate a difference signal, while the template signal for each subtraction is obtained by refinement processing of the most recently generated difference signal. If the repetitive subtraction process starts from an initial template signal that represents either the sequence of heart pulses or the sequence of pump pulses in the signal segment, consecutive difference signals will alternately approximate the sequence of pump pulses in the signal segment (when the difference signal is formed by subtraction of a template signal for the heart pulses) and the sequence of heart pulses in the signal segment (when the difference signal is formed by subtraction of a template signal for the pump pulses). The refinement processing aims at alternately cleaning up unwanted residuals from pump pulses and heart pulses, respectively, in the respective difference signal, so as to improve the accuracy of the template signal between the subtractions. This means, by this type of refinement processing, that both the difference signals and the template signals will gradually converge into a more and more accurate representation of the sequence of heart pulses and pump pulses, respectively, in the signal segment.

In one embodiment, the initial template signal approximates the sequence of pump pulses in the signal segment, with respect to both timing (location), magnitude and shape. It may be easier to obtain an approximate estimate of the pump pulses than the heart pulses in the signal segment, since the pump pulses typically dominate over the heart pulses in the signal segment. It is thus possible to estimate one or more of the timing, magnitude and shape of the pump pulses by processing the signal segment. Moreover, the reference signal REF may provide information about the timing of pump pulses.

The device 7 may be configured to execute a given number of subtractions on each signal segment in the pressure signal P, where the given number is at least two, so that the device 7 is operable to at least produce a refined template signal for the pump pulses. Alternatively, the device 7 may be configured to repeatedly execute the subtractions until a given convergence criterion is fulfilled, or until the number of subtractions exceed a predefined limit. The convergence criterion may detect that a sufficient separation of heart pulses and pump pulses is achieved.

Figure 5:
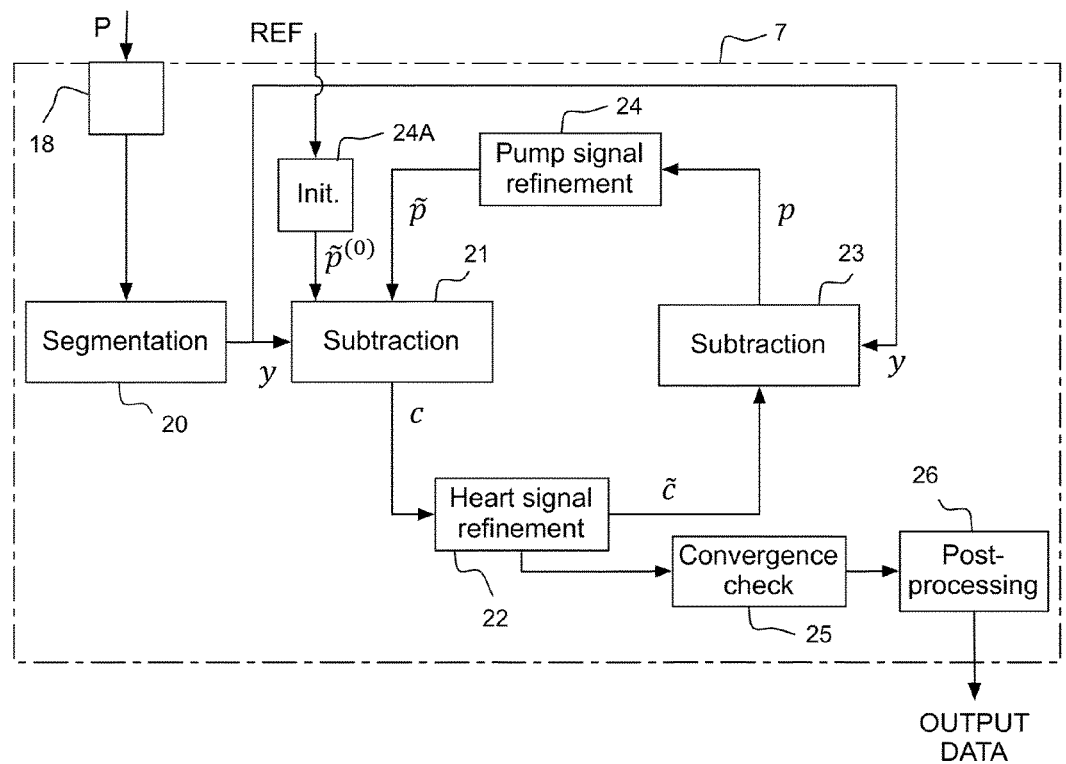
FIG. 5 is a block diagram of a filtering device according to one embodiment.

FIG. 5 is a block diagram for an embodiment of the device 7. The device 7 comprises an input block 18 configured to receive the pressure signal. The block 18 defines a communication interface of the device 7 and may be configured to pre-process the pressure signal P, e.g. by AD conversion, signal amplification, removal of offset, high frequency noise and supply voltage disturbances, etc. A segmentation block 20 is configured to extract a signal segment of predefined length in the pressure signal P. This signal segment, designated by y, is then processed iteratively to separate the heart and pump pulses that are contained within the signal segment y. A first subtraction block 21 acquires an initial template signal for the pump pulses, designated by $\tilde{p}^{(0)}$, from an initiation block 24A. The pump template signal $\tilde{p}^{(0)}$ is an initial estimate of the pump pulses within the signal segment, with respect to shape, magnitude and timing of the pump pulses. In the example of FIG. 5, the initiation block 24A is configured to generate $\tilde{p}^{(0)}$ based on the reference signal REF. The first subtraction block 21 is configured to subtract the pump template signal $\tilde{p}^{(0)}$ from the signal segment y so as to generate a first difference signal c. By way of the subtraction in block 21, the impact of the pump pulses is reduced in the first difference signal c compared to the signal segment y. The first difference signal c is therefore denoted "filtered heart signal" in the following. A first refinement block 22 is configured to acquire and process the filtered heart signal c so as to generate a template signal for the heart pulses, designated by $\tilde{c}$. The heart template signal $\tilde{c}$ is an estimate of the heart pulses within the signal segment, with respect to shape, magnitude and timing of the heart pulses. A second subtraction block 23 is configured to subtract the pump template signal $\tilde{c}$ from the signal segment y so as to generate a second difference signal p. By way of the subtraction in block 23, the impact of the heart pulses is reduced in the second difference signal p compared to the signal segment y. The second difference signal p is therefore denoted "filtered pump signal" in the following. A second refinement block 24 is configured to acquire and process the filtered pump signal p so as to generate a template signal for the pump pulses, designated by $\tilde{p}$. The updated pump template signal $\tilde{p}$ is supplied as input to the first subtraction block 21. The device 7 is then configured to sequentially operate the blocks 21-24 to generate updated versions of the signals c, $\tilde{c}$, p, $\tilde{p}$ until a convergence block 25 indicates that a predefined convergence criterion is fulfilled, which means that that heart pulses and pump pulses are sufficiently separated in one of more of the signals c, $\tilde{c}$, p, $\tilde{p}$. In the illustrated example, the convergence block 25 is configured to operate on the heart template signal $\tilde{c}$ to evaluate the convergence criterion. When the block 25 indicates that the convergence criterion is fulfilled, a post-processing block 26 is configured to generate the aforesaid output data, and the segmentation block 20 is configured to extract and provide another signal segment from the pressure signal P for iterative processing using blocks 21-24.

It should be understood that both the heart PH and the pump 4 are periodic (repetitive) pulse generators, i.e. they each produce a time-sequence of pulses in the pressure signal P. Thus, the pressure signal P may be regarded to contain a repeating sequence of "pump cycles" that each contain at least one pump pulse. Similarly, the pressure signal P may be regarded to contain a repeating sequence of "heart cycles" that each contain at least one heart pulse. As used herein, such a pump/heart cycle is manifested as a structure of a predetermined number of repeating pump/heart pulses in the pressure signal. It should be noted that the definition of a pump/heart cycle may be somewhat arbitrary, and a pump/heart cycle may contain any number of pump/heart pulses as long as each pump/heart pulse has a known or predictable location within the pump/heart cycle.

Reverting to the device in FIG. 5, it should be noted that the filtered heart signal c which is generated by the first subtraction block 21 in the first iteration contains residuals of pump pulses as well as noise. The task of the first refinement block 22 is to reduce the impact of signal components that originate from the pump 4. Similarly, the task of the second refinement block 24 is to reduce the impact of signal components that originate from the heart PH in the filtered pump signal p. In one embodiment, shown in FIGS. 6(a)-6(b), the refinement blocks 22, 24 are designed to make use of the fact that the filtered heart signal c and the filtered pump signal p includes a repeating sequence of heart cycles and pump cycles, respectively.

For the purpose of the inventive filtering technique, it may be desirable to set the pump cycle to represent the pulse generation process in the pump 4. For example, the peristaltic pump 4 in FIG. 3(a) generates two pump pulses for each revolution, and these pulses may differ from each other with respect to both timing, magnitude and shape since they represent pressure waves generated by different rollers 13a, 13b. With this pump 4, the pump cycle may be defined to represent two pump pulses, e.g. as shown in FIG. 3(b), or a multiple thereof. If the purpose of the filtering is to identify individual heart pulses, it may be desirable that the heart cycle is defined to represent a single heart pulse.

Figure 6A:
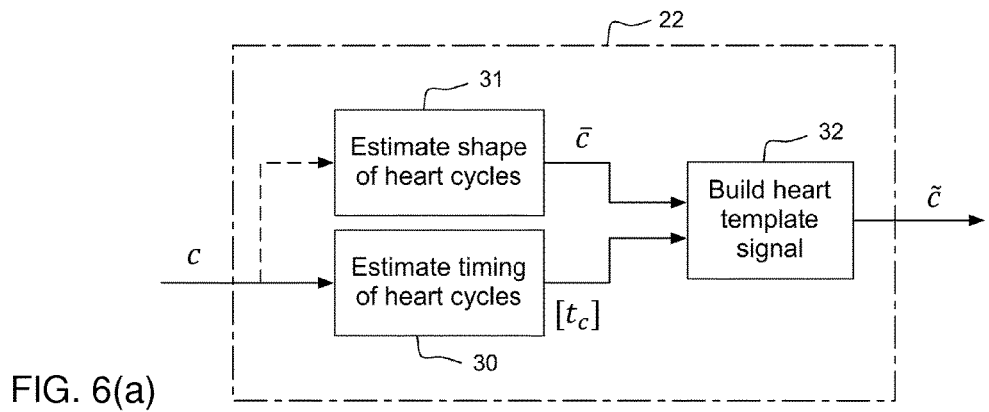
FIGS. 6(a)-6(b) are block diagrams of refinement blocks in FIG. 5 according to one embodiment.

Thus, the first refinement block 22 in FIG. 6(a) includes a timing detection block 30 which is configured to detect the heart cycles in the filtered heart signal c according to a predefined criterion and generate a reference time point for each heart cycle. Thus, block 30 is configured to process the filtered heart signal c for identification of a set of reference time points, collectively designated by $[t_c]$, within the signal segment. A shape estimation block 31 is configured to generate a heart cycle profile, designated by $\bar{c}$, which is an estimate of the shape (waveform) and magnitude of the heart cycle. As indicated by the dashed line, the profile $\bar{c}$ may but need not be generated by processing the filtered heart signal c. To generate the profile $\bar{c}$, block 31 may (but need not) use the reference time points $[t_c]$ determined by block 30. A combination block 32 is configured to build the heart template signal $\tilde{c}$ based on the set of reference time points $[t_c]$ and the heart cycle profile $\bar{c}$, by fitting one heart cycle profile $\bar{c}$ between each pair of consecutive reference time points. Thus, block 32 is configured to generate the heart template signal $\tilde{c}$ as a time sequence of heart cycle profiles $\bar{c}$ that are matched to the apparent timing of heart cycles in the filtered heart signal c.

Figure 6B:
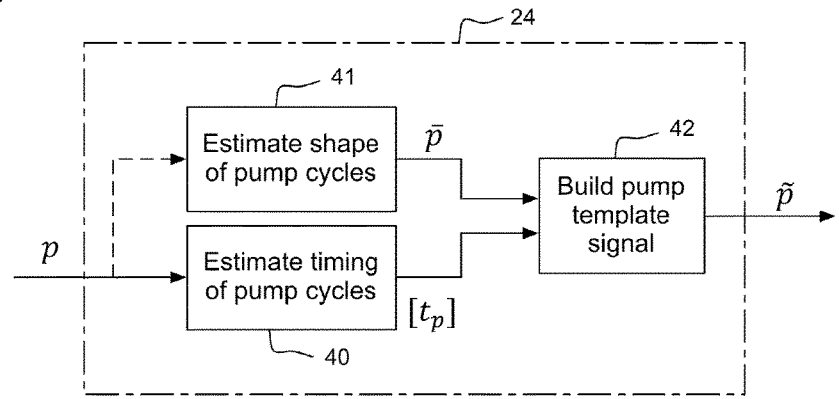

Similarly, the second refinement block 24 in FIG. 6(b) includes a timing detection block 40 which is configured to detect the pump cycles in the filtered pump signal p according to a predefined criterion and generate a reference time point for each pump cycle. Thus, block 40 is configured to process the filtered pump signal p for identification of a set of reference time points, collectively designated by $[t_p]$, within the signal segment. A shape estimation block 41 is configured to generate a pump cycle profile, designated by $\bar{p}$, which is an estimate of the shape (waveform) and magnitude of the pump cycle. To generate the profile $\bar{p}$, block 41 may (but need not) use the reference time points $[t_p]$ determined by block 40. A combination block 42 is configured to build the pump template signal $\tilde{p}$ based on the set of reference time points $[t_p]$ and the pump cycle profile $\bar{p}$, by fitting one pump cycle profile $\bar{p}$ between each pair of consecutive reference time points. Thus, block 42 is configured to generate the pump template signal $\tilde{p}$ as a time sequence of pump cycle profiles $\bar{p}$ with a timing that are matched to the apparent timing of pump cycles in the filtered pump signal p.

It is thus understood that the blocks 32, 42 are configured to concatenate or tile appropriately scaled cycle profiles at a given timing so as to produce a synthesized signal, which forms a best guess, for the current iteration, of how the heart pulses and pump pulses, respectively, appear in the signal segment y. The blocks 22, 24 are thereby operable to produce template signals $\tilde{c}$, $\tilde{p}$ that take into account shifts in apparent reference times $[t_c]$, $[t_p]$ in the filtered signals c, p caused by the subtraction of the template signals $\tilde{c}$, $\tilde{p}$ that were produced during the preceding iteration. The blocks 21-24 are thereby configured to stepwise, by each iteration, remove residuals of the pump pulses that remain in the filtered heart signal c (and thus also in the heart template signal $\tilde{c}$) and residuals of the heart pulses that remain in the filtered pump signal p (and thus also in the heart template signal $\tilde{p}$). In essence, this means that the device 7 is configured to iteratively refine the apparent reference time points $[t_c]$, $[t_p]$ for the heart and pump cycles while separating the heart pulses and the pump pulses into different signals.

Generally, the signal segment y is extracted, by block 20, to include at least two heart cycles and at least two pump cycles, so as to allow blocks 30, 40 to determine at least two reference times $[t_c]$, $[t_p]$ for each signal segment y. In this context, "at least two" does not imply two complete heart/pump cycles, only that the signal segment y spans more than one heart/pump cycle so that it is possible to detect at least two reference times for the pump cycles and the heart cycles, respectively, in the signal segment y. Thereby, blocks 32, 42 are operable to produce the template signals $\tilde{c}$, $\tilde{p}$ by matching at least one time-scaled cycle profile $\bar{c}$, $\bar{p}$ to the reference times $[t_c]$, $[t_p]$. However, in certain embodiments, it may be desirable for the signal segment y to include a larger number of heart cycles and pump cycles, e.g. if the cycle profiles $\bar{c}$, $\bar{p}$ are determined by detecting and averaging a plurality of apparent cycles in the signal segment y. In such embodiments, it may be desirable for the signal segment y to include at least 5 and more preferably at least 10 heart cycles and pump cycles, respectively.

The operation of the filtering device 7 will now be described in further detail with reference to the flow chart in FIG. 7 which shows an embodiment of an inventive method for separating heart pulses and pump pulses. The steps S1-S12 of the method in FIG. 7 will be explained and exemplified with reference to example signals in FIGS. 8(a)-8(g). The example signals are generated by iterative processing according to an Implementation Example, which will be described further below.

As noted, the method produces signals c, p, as well as signals $\tilde{c}$, $\tilde{p}$ for each iteration. To distinguish these signals in the following description, a superscript j has been added within parenthesis to indicate the current iteration, where j is incremented from zero. For example, $p^{(0)}$ represents the filtered pump signal generated during the first iteration.

It should be noted that all example signals presented herein have been generated by processing a simulated pressure signal. The use of a simulated pressure signal makes it possible to evaluate embodiments of the inventive filtering for many different combinations of blood flow rates (pump pulse rates), heart pulse rates, pump pulse amplitudes and heart pulse amplitudes. Further, by using simulated signals it is possible to compare the signals c, p, c̃, p̃ that are produced by the inventive filtering with the actual heart pulses and pump pulses that are embedded in the simulated pressure signal.

The simulated pressure signal was built from a combination of three simulated signals: a pump signal, a heart signal and measurement noise signal. The simulated pump signal was generated based on a pressure signal recorded in a laboratory setting that simulates an actual dialysis system without any physiological signals present. Representative pump cycle profiles corresponding to one full revolution of a peristaltic pump (FIG. 3(a)) were generated by averaging at blood flow rates from 20-500 ml/min in steps of 10 ml/min. The time resolution of the pump cycle profiles was 0.001 s. A simulated pump signal of selectable length was then synthesized by adding/stacking re-sampled pump cycle profiles of varying duration after each other. The varying duration was simulated as white Gaussian noise with the same standard deviation as observed for the current blood flow rate. The simulated heart signal was generated using frequency modulation (FM). In order to get a power spectral density (PSD) similar to that of a human heart, white Gaussian noise was colored by filter parameters according to an autoregressive model disclosed in the article "*Improved heart rate variability signal analysis from the beat occurrence times according to the IPFM model*", by J. Mateo and P. Laguna, published in IEEE Trans. Biomed. Eng., vol. 47, pp 997-1009, 2000. The colored noise was used as frequency modulating input m(t) for the FM model:

$$c_{sim}(t) = \sum_{l=1}^{L} \alpha_l \cos(2\pi l F_0 g(t) + \phi_l)$$

with $$g(t) = t + \frac{1}{m_{max}} \int_0^t m(\tau) d\tau$$

where $F_0$ is the average heart rate, and $m_{max}$ is the maximum value of the integral of m(t), L=2, $\phi_1$=0, $\phi_2$=0.01, $\alpha_1$=1 and $\alpha_2$=0.25. The measurement noise signal was simulated by white Gaussian noise with a standard deviation of 0.15 mmHg.

Figure 7:
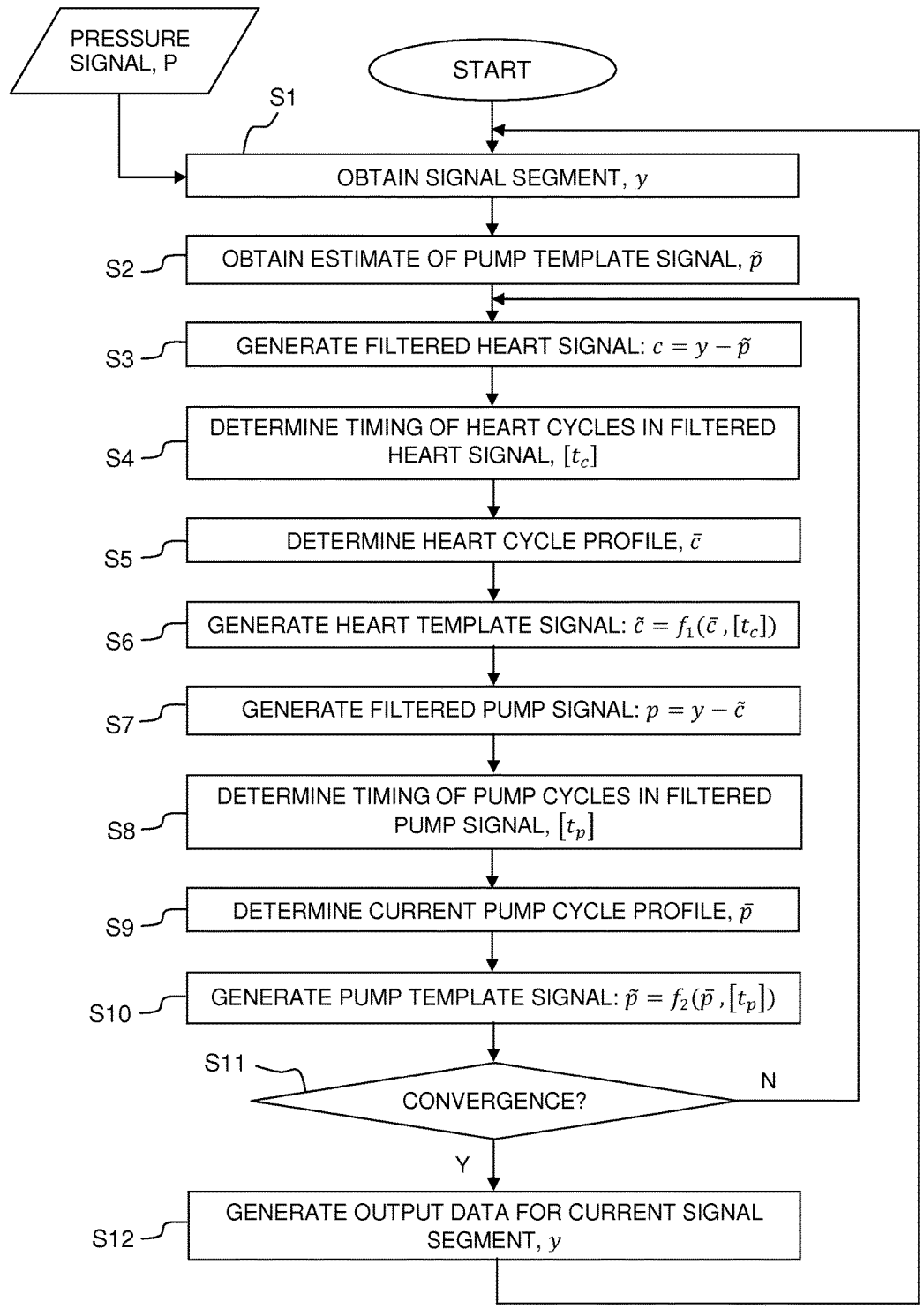
FIG. 7 is a flow chart of a method of filtering a pressure signal that may be implemented by the filtering device in FIGS. 5-6.

The method in FIG. 7 comprises an outer loop that repeatedly extracts a signal segment y from the pressure signal P, by step S1, and an inner loop, that processes the respective signal segment y for separation of heart pulses and pump pulses, by an initiation step S2 followed by one or more iterations of steps S3-S11.

Step S1 is implemented by block 20 in FIG. 5. In one implementation, the device 7 is configured to buffer the pressure signal P in internal memory (cf. 9b in FIG. 1), and step S1 extracts the signal segments y from the memory. Each signal segment y corresponds to a predefined time window in the pressure signal and comprises a time sequence of signal values (pressure values). The time window may be selected to contain a plurality of heart cycles and a plurality of pump cycles. The length of the time window may be pre-defined and fixed, or it may be adapted based on the current operating frequency of the pump 4, e.g. as given by the reference signal REF. Step S1 may extract the signal segments to be consecutive and non-overlapping in the pressure signal P, which may improve the speed at which output data is generated by the method. Alternatively, the signal segments y may be partially overlapping in the pressure signal P, which may improve the accuracy of the generated output data. The length of the time window as well the choice between overlapping and non-overlapping segments may be different for different types of output data.

In step S2 (implemented by block 24A in FIG. 5), an initial estimate of the pump template signal $\tilde{p}^{(0)}$ is either generated or acquired from memory. The initial signal $\tilde{p}^{(0)}$ is obtained as an initial best guess of the shape, magnitude and timing of the pump cycles in the current signal segment y. In one embodiment, step S2 generates the initial signal $\tilde{p}^{(0)}$ by acquiring an estimate of the expected timing of pump cycles in the current signal segment y, as well as an estimate of the current pulse cycle profile, i.e. the expected shape and magnitude of pulse cycles in the current signal segment y. Step S2 may then form the initial signal $\tilde{p}^{(0)}$ by assembling a sequence of the pulse cycle profiles one after the other at the expected timing. Various embodiments for acquiring and assembling such pulse cycle profiles are described below with reference to steps S8-S10. The estimate of the expected timing of pump cycles may be acquired from the reference signal REF (as indicated in FIG. 5), or by processing the signal segment y, e.g. using the techniques described below in relation to step S8. An iterative approach for computing a more precise estimate of the reference times from the signal segment y, as well as for generating the current pulse cycle profile, is disclosed in the Implementation Example.

In an alternative embodiment, which requires a larger memory capacity, the device 7 associates pumping frequencies with different pump template signals stored in the memory of the device. Step S2 obtains an estimate of the current pumping frequency, e.g. from the reference signal REF or by processing the signal segment y, and then directly acquires the entire signal $\tilde{p}^{(0)}$ from the memory based on the current pumping frequency.

In yet another embodiment, the device 7 retrieves the initial signal $\tilde{p}^{(0)}$ based on one of the signals that were generated by the method in the processing of a preceding signal segment. For example, step S2 may set the initial signal $\tilde{p}^{(0)}$ equal to the pump template signal p̃ that was generated by step S10 or the filtered pump signal p that was generated by step S7 when the preceding signal segment was processed iteratively by steps S3-S11. Alternatively, step S2 may generate the initial signal $\tilde{p}^{(0)}$ as a function of the reference time points $[t_p]$ and the pump cycle profile $\bar{p}$ generated by steps S8 and S9. For example, an average cycle length may be estimated from the reference time points $[t_p]$, and the initial signal $\tilde{p}^{(0)}$ may be generated by tiling (cf. step S10) time-scaled versions the pump cycle profile $\bar{p}$ so as to match the average pulse cycle length.

Figure 8A:
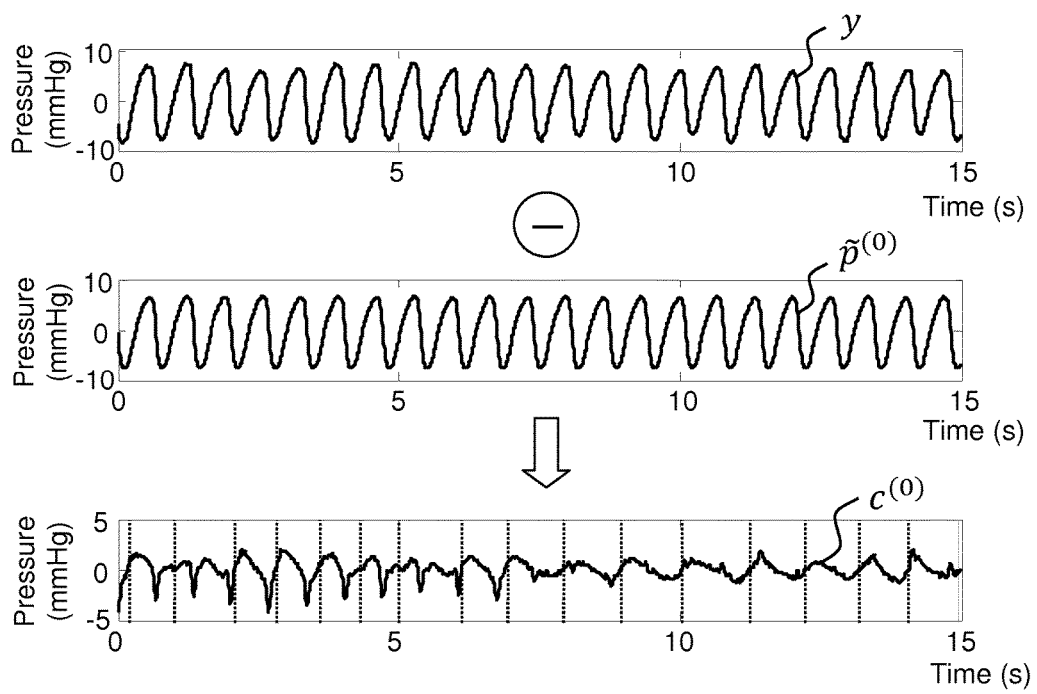
FIGS. 8(a)-8(g) illustrate signals generated during a first iteration of the method in FIG. 7 in one exemplifying implementation.

In step S3 (implemented by block 21 in FIG. 5), the initial signal $\tilde{p}^{(0)}$ is aligned with and subtracted from the signal segment y, as shown in FIG. 8(a), to generate the filtered heart signal $c^{(0)}$ for the first iteration. In FIG. 8(a), the signal $c^{(0)}$ coarsely represents the heart pulses in the signal segment but also includes significant interference from pump pulses and measurement noise. In a variant, not shown, step S3 applies a low-pass or band-pass filter to the filtered heart signal $c^{(0)}$ to reduce noise and residuals of pump pulses, so as to potentially improve the accuracy of the reference times that are determined by step S4 (below).

Figure 8B:
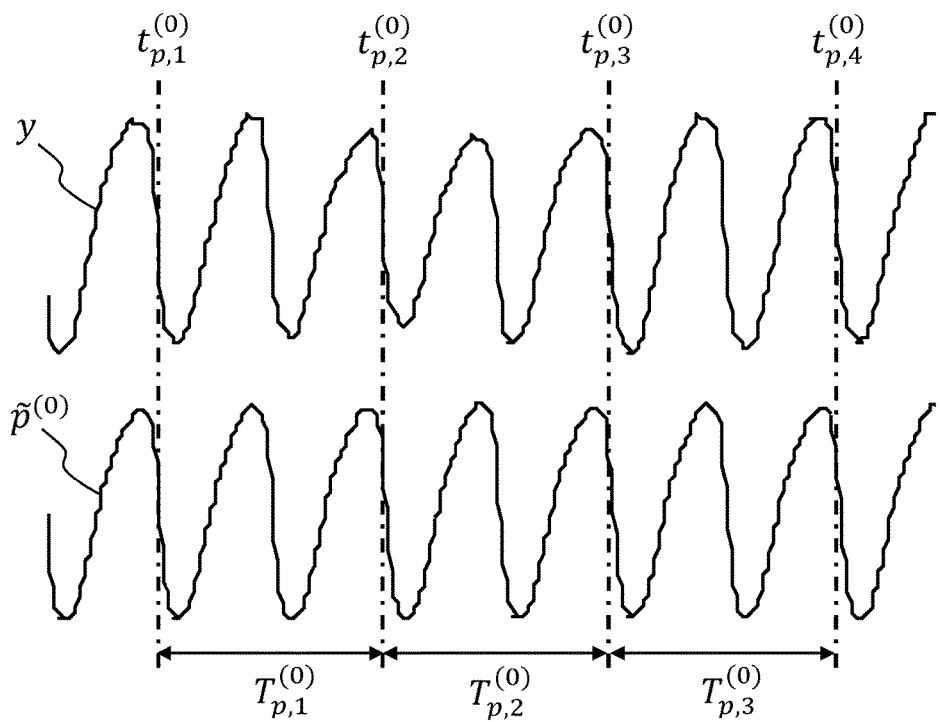

The alignment in step S3 may be achieved by matching at least one reference time in the signal segment y to a corresponding reference time in the initial signal $\tilde{p}^{(0)}$, or by fitting the signal segment y to the initial signal $\tilde{p}^{(0)}$, e.g. by correlation. The reference time may be given by any signal feature which is identifiable in both the signal segment y and the initial signal $\tilde{p}^{(0)}$. FIG. 8(b) is an enlarged view of the signal segment y and the initial signal $\tilde{p}^{(0)}$ in FIG. 8(a). In this example, reference times in the signal segment are aligned with reference times in the initial signal $\tilde{p}^{(0)}$. In this example, each reference time $t_{p,k}^{(0)}$ (k=1-4) is determined to represent the location of an individual pump cycle. In FIG. 8(b), the double-ended arrows $T_{p,k}^{(0)}$ (k=1, 2, 3) indicate the estimated cycle length of each individual pump cycle. The alignment between signals is typically only determined in the first execution of step S3 during the iterative processing of the current signal segment y.

Figure 8C:
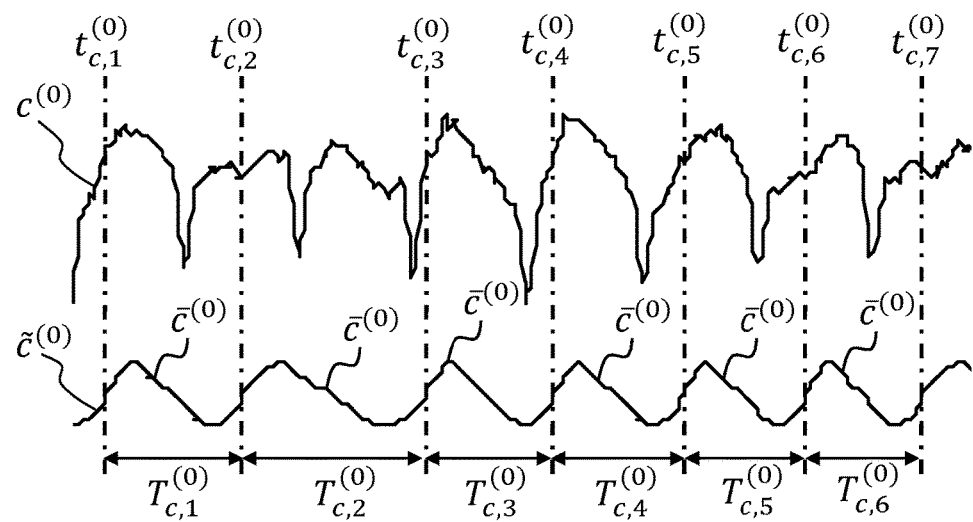

The top curve in FIG. 8(c) is an enlarged view of the filtered heart signal $c^{(0)}$ at the bottom of FIG. 8(a). Steps S4-S6 (implemented by block 22 in FIG. 5) operate to process the filtered heart signal $c^{(0)}$ for generation of the heart template signal $\tilde{c}^{(0)}$, by retaining a timing of apparent heart cycles in the filtered heart signal $c^{(0)}$ and by replacing the apparent heart cycles with heart cycle profiles $\bar{c}^{(0)}$. First, step S4 (cf. block 30 in FIG. 6(a)) determines the timing of apparent heart cycles in the signal $c^{(0)}$, by determining reference times according to a predefined criterion. These reference times are represented by dashed vertical lines in FIG. 8(a), and in FIG. 8(c) the seven first reference times are designated by $t_{c,k}^{(0)}$ (k=1-7). The criterion is selected with knowledge of the general shape of the heart cycles so as to consistently generate one reference time point for each heart cycle. For example, the criterion may detect and assign a respective reference time to the zero crossings, the maximum values, or the minimum values in the filtered heart signal $c^{(0)}$. By determining the reference times, step S4 also implicitly determines the cycle lengths of the apparent heart cycles, designated by $T_{c,k}^{(0)}$ (k=1-6) in FIG. 8(c).

Figure 8D:
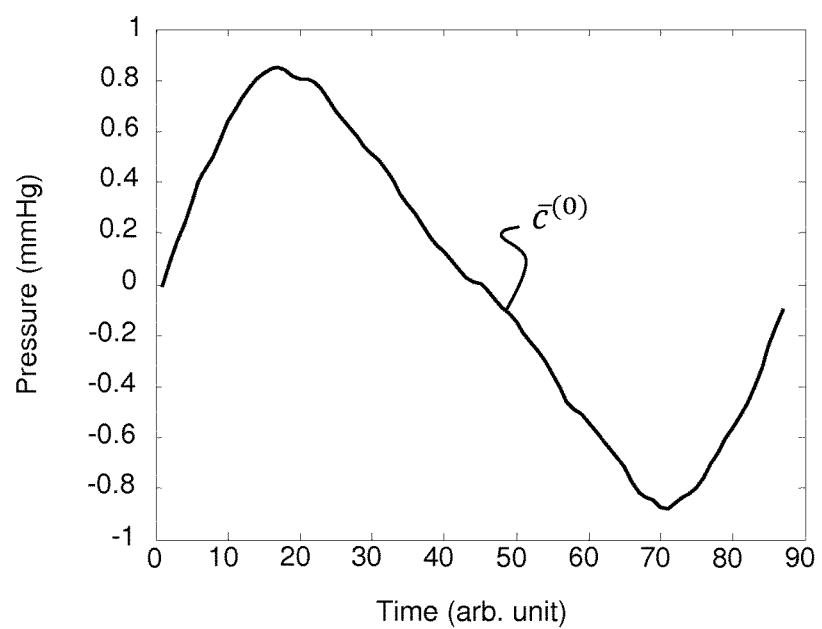

Then, step S5 (cf. block 31 in FIG. 6(a)) determines a current heart cycle profile $\bar{c}^{(0)}$ for each heart cycle in the signal $c^{(0)}$. An example of a heart cycle profile $\bar{c}^{(0)}$ is shown in FIG. 8(d). Step S5 may be implemented in many ways to determine the profile $\bar{c}^{(0)}$. In a first main variant, step S5 uses a fixed heart cycle profile, which may be predetermined for a selected subject, a group of subjects or all subjects and is fixed throughout the filtering process. The fixed profile may be pre-generated in a reference measurement. Such a reference measurement may operate on a pressure signal that is acquired in the current EC circuit and/or another EC circuit when connected to a subject, while the blood pump is stopped, and the fixed profile may be generated by detecting and averaging heart cycles in the pressure signal. Optionally, such a pre-generated profile may be adapted to specifics of the current EC circuit, by applying a mathematical model taking into account arrangement-specific parameters, such as type of vascular access, connection system, flow rate, fluid characteristics, etc. In a specific variant, the reference measurement is performed at start-up of the EC circuit 1, e.g. during priming, or at one or more instances when the EC circuit 1 has been operated to draw blood from the subject, e.g. at start-up of the method in FIG. 7. Thereby, the fixed profile is generated to be specific to the subject as connected to the current EC circuit. Alternatively, the fixed profile may be obtained entirely by mathematical modeling for a selected type of EC circuit. According to yet another alternative, the fixed profile is a standard curve/function, e.g. a sinusoid or a bell-shaped function such as a Gaussian distribution function. In a second main variant, step S5 acquires a heart cycle profile which is adapted to the current operating condition of the EC circuit, e.g. the current pumping frequency (blood flow rate). The adapted profile may be acquired from a library of heart cycle profiles that are associated with different operating conditions and stored in memory. The heart cycle profiles in the library may be generated in the same way as the above-mentioned fixed profiles, e.g. by mathematical modeling, by a reference measurement, or a combination thereof. Alternatively, the adapted profile may be generated during execution of the method in FIG. 7, by intermittently causing a controller (not shown) in the EC circuit 1 to stop the blood pump 4 and by detecting and averaging heart cycles in a pressure signal acquired from the EC circuit 1. This pressure signal may, but need not, be the same pressure signal P that is processed for separation of heart and pump pulses. In the example of FIG. 1, the heart cycle profiles may be generated by processing the arterial pressure signal from sensor 6a, while the venous pressure signal P from sensor 6b is processed for separation of heart and pump pulses. In a further variant, the adapted profile is generated by processing the filtered heart signal $c^{(0)}$ for detection and averaging of apparent heart cycles, e.g. in analogy with the generation of the pump cycle profile as described below with reference to FIG. 9.

An iterative approach that repeatedly executes steps S4 and S5 to estimate the reference times in the filtered heart signal $c^{(0)}$ and to generate the current heart cycle profile $\bar{c}^{(0)}$ from the filtered heart signal $c^{(0)}$ is disclosed in the Implementation Example.

Subsequent to steps S4 and S5, step S6 (cf. block 32 in FIG. 6(a)) generates the heart template signal $\tilde{c}^{(0)}$ as a function of the reference times from step S4 and the heart cycle profile $\bar{c}^{(0)}$ from step S5. In one embodiment, the heart template signal $\tilde{c}^{(0)}$ is generated as a sequence of time-scaled versions of the current heart cycle profile $\bar{c}^{(0)}$. As exemplified in FIG. 8(c), profiles $\bar{c}^{(0)}$ are time-scaled and concatenated (tiled one after the other) so as to match the reference times in the filtered heart signal $c^{(0)}$. As shown, the heart template signal $\tilde{c}^{(0)}$ is generated to contain one heart cycle profile $\bar{c}^{(0)}$ for each cycle length $T_{c,k}^{(0)}$, (k=1-6) in the filtered heart signal $c^{(0)}$. In a variant, the heart cycle profile $\bar{c}^{(0)}$ is scaled in both time and amplitude to match the signal values within the respective cycle length $T_{c,k}^{(0)}$ in the filtered heart signal $c^{(0)}$.

Should the subject experience cardiac dysrhythmia during the recording of the pressure signal P, e.g. by occurrence of ectopic beats, one or more of the heart cycles in the signal segment may (but need not) have a waveform that deviates from the "normal" waveform of heart cycles, which is represented by the current heart cycle profile $\bar{c}^{(0)}$. Depending on the magnitude of the deviation, significant errors may be introduced if step S6 replaces such a deviating heart cycle with a time-scaled version of the profile $\bar{c}^{(0)}$. In one embodiment, which ameliorates this potential problem, step S6 selects the heart cycle profile to be time-scaled and concatenated for each pulse cycle, among a plurality of candidate profiles, based on the apparent cycle length of the respective pulse cycle. For example, if step S6 determines that the apparent pulse cycle length for a given pulse cycle is larger or smaller than a normal time range, it may select a dedicated deviating heart profile to be time-scaled and inserted at the given pulse cycle instead of the profile $\bar{c}^{(0)}$ that is generated by step S4. Step S4 may associate different non-normal time ranges with different deviating heart profiles, which may be pre-generated by mathematical modeling, by a reference measurement, or a combination thereof.

In another variant, steps S4 and S5 are omitted and step S6 calculates the respective signal value in the heart template signal $\tilde{c}^{(0)}$ (at each time point $t_m$) as a weighted combination of at least two adjacent signal values in the filtered heart signal $c^{(0)}$ (e.g. at times $t_{m-1}$ and $t_{m-2}$, or at times $t_{m-1}$ and $t_{m+1}$). Such a technique of generating the heart template signal $\tilde{c}^{(0)}$ corresponds to the "proximity prediction approach" which is disclosed in WO2013/000777, albeit for estimating the contribution of pump pulses in a pressure signal. It lies within the reach of the skilled person to adapt any of the embodiments of the proximity prediction approach for generating the heart template signal $\tilde{c}^{(0)}$. It should be noted that in this variant, step S6 does not involve concatenation of heart cycle profiles.

Figure 8E:
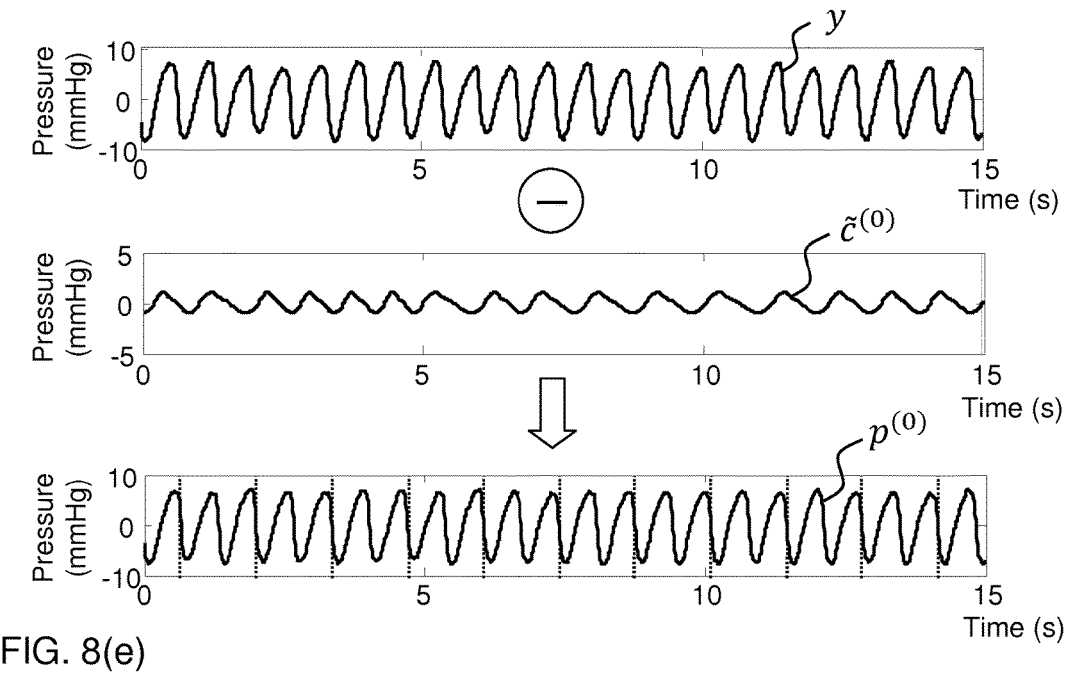

In step S7 (implemented by block 23 in FIG. 5), the heart template signal $\tilde{c}^{(0)}$ is aligned with and subtracted from the signal segment y, as shown in FIG. 8(e), to generate the filtered pump signal $p^{(0)}$ for the first iteration.

Although the signal $p^{(0)}$ approximates the pump pulses in the signal segment y, it is also likely to include residuals from heart pulses as well as noise. In a variant, not shown, step S7 applies a low-pass or band-pass filter to the filtered pump signal $p^{(0)}$ for noise reduction, so as to potentially improve the accuracy of the reference times that are determined by step S8 (below).

Figure 8F:
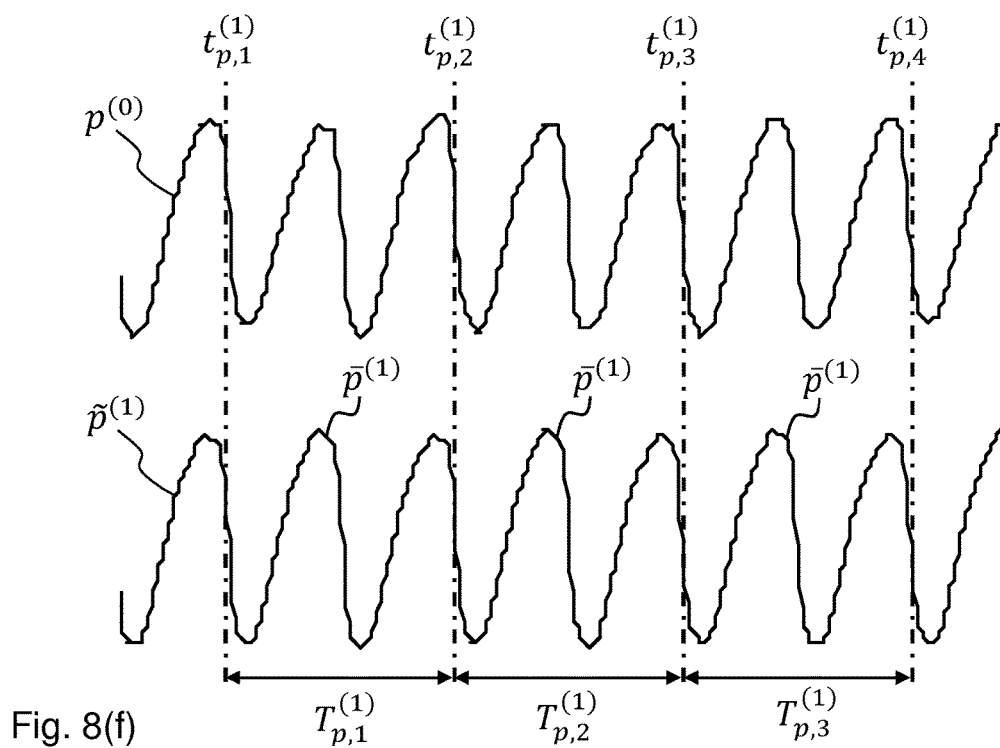

The top curve in FIG. 8(f) is an enlarged view of the filtered pump signal $p^{(0)}$ at the bottom of FIG. 8(e). Steps S8-S10 (implemented by block 24 in FIG. 5) operate to process the filtered pump signal $p^{(0)}$ for generation of the pump template signal $\tilde{p}^{(1)}$, by retaining a timing of apparent pump cycles in the filtered pump signal $p^{(0)}$ and by replacing the apparent pump cycles with the pump cycle profiles $\bar{p}^{(1)}$. First, step S8 (cf. block 40 in FIG. 6(b)) determines the timing of the apparent pump cycles in the signal $p^{(0)}$, by determining reference times according to a predefined criterion. These reference times are represented by dashed vertical lines in FIG. 8(e), and in FIG. 8(f) the four first reference times are designated by $t_{p,k}^{(1)}$ (k=1-4). The criterion is selected with knowledge of the general shape of the pump cycles so as to consistently generate one reference time point for each pump cycle. For example, the criterion may detect and assign a respective reference time to selected zero crossings, maximum values, or minimum values in the filtered pump signal $p^{(0)}$. Alternatively, the reference time points may be determined from the reference signal REF. By determining the reference times, step S8 also implicitly determines the cycle lengths of the apparent pump cycles, designated by $T_{p,k}^{(1)}$ (k=1-3) in FIG. 8(f).

Figure 8G:
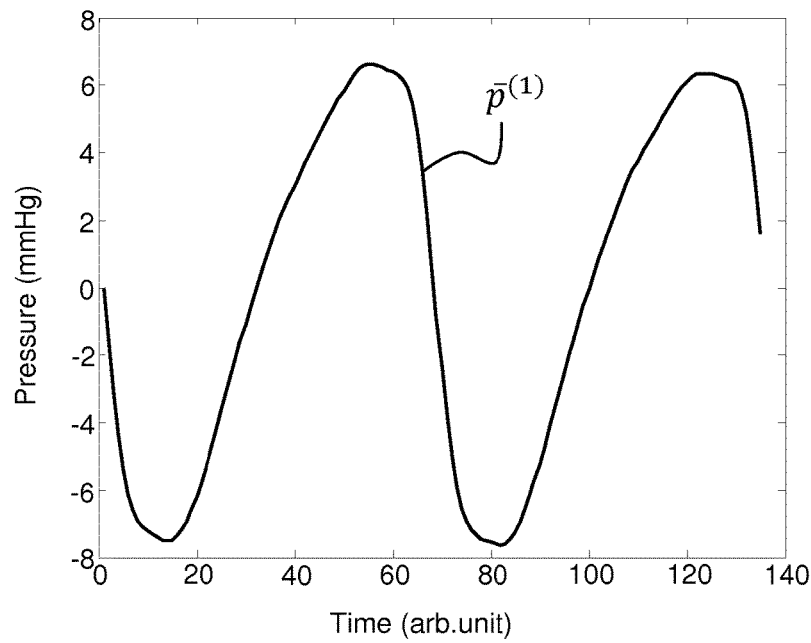
Figure 9:
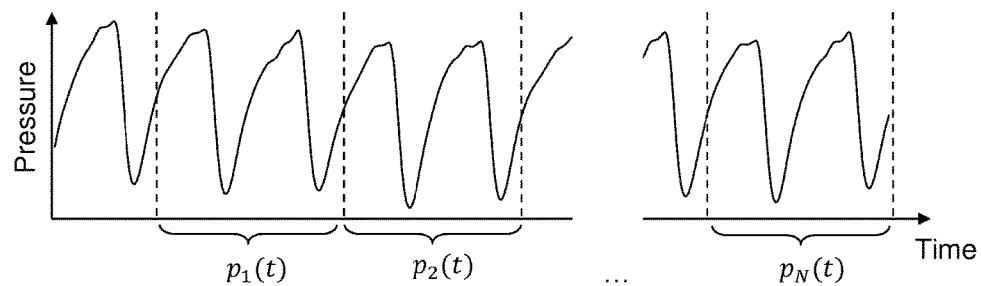
FIG. 9 illustrate generation of a pump cycle profile by averaging of pump cycles in a pressure signal.
Figure 9:
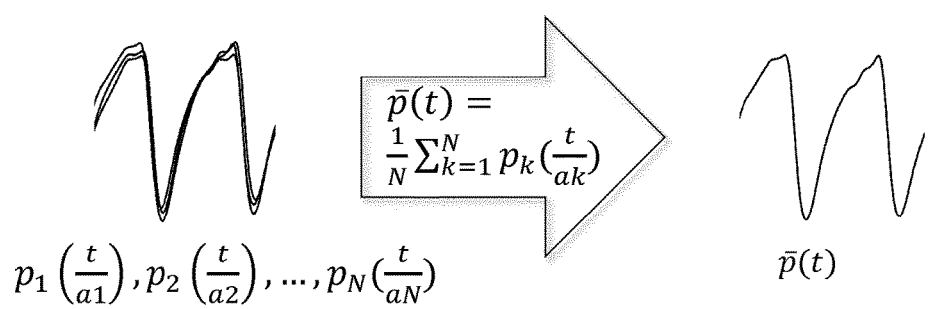

Then, step S9 (cf. block 41 in FIG. 6(b)) determines a current pump cycle profile $\bar{p}^{(1)}$ for each pump cycle in the signal $p^{(0)}$. An example of a pump cycle profile $\bar{p}^{(1)}$ is shown in FIG. 8(g). Step S9 may be implemented in many ways to determine the profile $\bar{p}^{(1)}$. In a first main variant, step S9 uses a fixed pump cycle profile, which may be predetermined for the current EC circuit or a group of EC circuits and is fixed throughout the filtering process. The fixed profile may be pre-generated in a reference measurement. Such a reference measurement may operate on a pressure signal that is acquired in the current EC circuit and/or another EC circuit, and the fixed profile may be generated by detecting and averaging pump cycles in the pressure signal. FIG. 9 schematically shows an example of such averaging, in which a number of apparent pump cycles $p_1(t)$-$p_N(t)$, which are identified in the pressure signal, are re-scaled to equal cycle length by applying a respective time scale factor $a_1$-$a_N$ and then averaged into a profile $\bar{p}(t)$. Although the average is represented as an arithmetic mean in FIG. 9, the respective signal value of the profile $\tilde{p}(t)$ may be generated as any known measure of central tendency of corresponding signal values in the apparent pump cycles $p_1(t)$-$p_N(t)$. The reference measurement may be implemented such that the pressure signal is free of heart pulses, e.g. in a laboratory setting. Alternatively, the pressure signal may contain heart pulses, provided that the magnitude of the heart pulses are small compared to the pump pulses and that the rate of heart pulses differ from all of the harmonic frequencies of the pump 4. Optionally, such a pre-generated profile may be adapted to specifics of the current EC circuit, by applying a mathematical model taking into account arrangement-specific parameters, such as type of vascular access, connection system, flow rate, fluid characteristics, etc. In a specific variant, the reference measurement is performed at start-up of the EC circuit 1, e.g. during priming, or at one or more times when the EC circuit 1 has been operated to draw blood from the subject, e.g. at start-up of the method in FIG. 7. Thereby, the fixed profile is generated to be specific for the current EC circuit 1. Alternatively, the fixed profile may be obtained entirely by mathematical modeling for a selected type of EC circuit. In a second main variant, step S9 acquires a pump cycle profile which is adapted to the operating condition of the EC circuit during the current iteration, e.g. the pumping frequency. The adapted profile may be acquired from a library of pump cycle profiles that are associated with different operating conditions and stored in memory. The pump cycle profiles in the library may be generated in the same way as the above-mentioned fixed profiles, e.g. by mathematical modeling, by a reference measurement, or a combination thereof. Alternatively, the adapted profile may be generated during execution of the method in FIG. 7, by detecting and averaging pump cycles in a pressure signal from the EC circuit 1, e.g. as described above with reference to FIG. 9. This pressure signal may, but need not, be the same pressure signal P that is processed for separation of heart and pump pulses. In the example of FIG. 1, the pump cycle profile may be generated by processing a pressure signal from a "system pressure sensor" (not shown) which may be installed between the pump 4 and the blood processing unit 5, e.g. in certain types of dialysis systems. The pressure signal from such a system pressure sensor is dominated by pump pulses. In another example, the adapted profile is generated by processing the filtered pump signal $p^{(0)}$ for detection and averaging of apparent pump cycles, e.g. as described above with reference to FIG. 9. Each signal value in such an adapted profile may be generated using any one of the techniques for identifying and combining cycle-synchronized data samples as disclosed in WO2013/000777, which is incorporated herein by reference.

An iterative approach that repeatedly executes steps S8 and S9 to estimate the reference times in the filtered pump signal $p^{(0)}$ and to generate the current pump cycle profile $\bar{p}^{(1)}$ from either the filtered pump signal $p^{(0)}$ or the current signal segment y is disclosed in the Implementation Example. This iterative approach may be repeated intermittently during execution of the method, e.g. for every iteration of steps S3-S11, to generate an adapted profile, or only once, e.g. by step S9 at start-up of the method to generate a fixed profile.

Subsequent to steps S8 and S9, step S10 (cf. block 42 in FIG. 6(b)) generates the pump template signal $\tilde{p}^{(1)}$ as a function of the reference times from step S8 and the pump cycle profile $\bar{p}^{(1)}$ from step S9. In one embodiment, the pump template signal $\tilde{p}^{(1)}$ is generated as a sequence of time-scaled versions of the current pump cycle profile $\bar{p}^{(1)}$. As exemplified in FIG. 8(f), profiles $\bar{p}^{(1)}$ are time-scaled and concatenated (tiled one after the other) so as to match the reference times in the filtered pump signal $p^{(0)}$. As shown, the pump template signal $\tilde{p}^{(1)}$ is generated to contain one pump cycle profile $\bar{p}^{(1)}$ for each cycle length $T_{p,k}^{(0)}$, (k=1-3) in the filtered pump signal $p^{(0)}$. In a variant, the pump cycle profile $\bar{p}^{(1)}$ is scaled in both time and amplitude to match the signal values within the respective cycle length $T_{c,k}^{(0)}$ in the filtered pump signal $p^{(0)}$.

In certain embodiments, step S8 may be omitted if the pump is known to generate pump cycles with an essentially equal cycle length, e.g. when the pump rate can be expected not to change significantly within a signal segment. Under these circumstances, step S8 may instead determine the current average rate of pump cycles, and thereby an average cycle length, which allows step S10 to scale (if necessary) the pump cycle profile provided by step S9 to the average cycle length and concatenate such pump cycle profiles. The current average rate of pump cycles may be determined based on the reference signal REF, or by analysis of the current signal segment y or the filtered pump signal $p^{(0)}$.

In a further variant, both of steps S8 and S9 are omitted, and step S10 directly generates the pump template signal $\tilde{p}^{(1)}$ as a sum of sinusoids at a plurality of different frequencies. Each of the sinusoids may have a length equal to the signal segment y and a frequency equal to a respective harmonic frequency ($0.5f_0$, $f_0$, $1.5f_0$, $2f_0$, etc) of the blood pump 4. This variant is based on the insight that the pump pulses in the signal segment y are formed as a combination of sinusoids at the harmonic frequencies (cf. FIG. 2(b)). The harmonic frequencies may be determined based on the current rate of pump cycles. It should be noted that in this variant, step S10 does not involve concatenation of pump cycle profiles. As a related matter, WO2014/009111 discloses a processing-efficient technique for combining sinusoids into an estimated pump signal, by correlating the respective sinusoid with a signal segment in a pressure signal to generate a respective correlation value, and then generating the estimated pump signal as a linear combination of the sinusoids weighted by the respective correlation value. The technique and its various implementations as disclosed in WO2014/009111 may thus be implemented in step S10 for generating the pump template signal $\tilde{p}^{(1)}$. WO2014/009111 is incorporated herein by reference.

In another variant, in which steps S8 and S9 likewise are omitted, step S10 predicts the respective signal value in the pump template signal $\tilde{p}^{(1)}$ (at time $t_m$) as a weighted combination of at least two adjacent signal values in the filtered pump signal $p^{(0)}$ (e.g. at times $t_{m-1}$ and $t_{m-2}$, or at times $t_{m-1}$ and $t_{m+i}$). This technique of generating the pump template signal $\tilde{p}^{(1)}$ corresponds to the above-mentioned "proximity prediction approach" as disclosed in WO2013/000777. It should be noted that in this variant, step S10 does not involve concatenation of heart cycle profiles. It should also be noted that any one of the above-described techniques for generating the pump template signal $\tilde{p}^{(1)}$ according to steps S8-S10 (including the variants without step S8 and the variants without steps S8-S9) may be applied by step S2 to generate the initial estimate $\tilde{p}^{(0)}$, by processing the current signal segment y.

In step S11 (implemented by block 25 in FIG. 5), the method evaluates a convergence criterion, e.g. by generating a convergence parameter value and by comparing this value to a threshold or range. The convergence criterion may be deemed fulfilled if the convergence parameter value has a proper value during a given number of iterations (at least one). If the convergence criterion is fulfilled, the method proceeds to step S12 for generation of output data, otherwise the method proceeds to step S3 for a new iteration (to generate signals $c^{(1)}$, $\tilde{c}^{(1)}$, $p^{(1)}$ and $\tilde{p}^{(2)}$). It should be noted that the convergence check in step S11 may be executed at any time during the sequence of steps S3-S10.

The convergence criterion is selected to indicate that the heart and pump pulses have been sufficiently separated, and may involve calculation and evaluation of one or more of the following convergence parameters.

In a first type of convergence criterion, the convergence parameter represents a correspondence in timing between the current iteration and a preceding iteration. In one example, the convergence parameter represents a difference in the timing of pump cycles between consecutive iterations and may be calculated by, e.g., analyzing the reference times $[t_p]$ determined by step S8. In another example, the convergence parameter represents a difference in the timing of heart pulses between consecutive iterations and may be calculated by, e.g., analyzing the reference times $[t_c]$ determined by step S4. The convergence parameter may be calculated to compare the reference times in ordered pairs between the consecutive iterations, such that the first reference time in the current iteration is compared with the first reference time in the preceding iteration, etc. In yet another example, the convergence parameter represents a difference in the timing of pump cycles determined by the method compared to the timing of pump cycles indicated by the reference signal REF. In all of these examples, the convergence parameter may be any measure that consistently represents the difference (or similarity) between the pairs of reference times, including the maximum difference, a sum of absolute differences, a sum of squared differences, the mean value, the median value, etc.

In a second type of convergence criterion, the convergence parameter represents a correspondence in shape between the current iteration and a preceding iteration. In one example, the convergence parameter represents a difference between consecutive iterations in the shape of the pump template signal $\tilde{p}$ generated by step S10, or the filtered pump signal p generated by step S7. In another example, the convergence parameter represents a difference between consecutive iterations in the shape of the heart template signal $\tilde{c}$ generated by step S6, or the filtered heart signal c generated by step S3. In these examples, the convergence parameter may be given by any measure that consistently represents the difference (or similarly) between two curves. For example, the convergence parameter may be calculated to represent the pair-wise difference between the signal values at each time step in the two curves, e.g. by the maximum difference, the sum of absolute differences, the sum of squared differences, the mean value of the differences, the median value of the differences, correlation value, correlation coefficient, etc.

In a third type of convergence criterion, the convergence parameter represents a correspondence in shape between corresponding signals generated during one iteration, e.g. pump template signal $\tilde{p}$ and the filtered pump signal p, or the heart template signal $\tilde{c}$ and the filtered heart signal c. This also amounts to comparing two curves, and the convergence parameter may be given by any of the measures listed above for the second type of convergence criterion.

In a fourth type of convergence criterion, the convergence parameter value represents the difference (or similarity) in shape between the signal segment y and the sum of the pump template signal $\tilde{p}$ and the heart template signal $\tilde{c}$, or alternatively, the sum of the filtered pump signal p and the filtered heart signal c. This also amounts to comparing two curves, and the convergence parameter may be given by any of the measures listed above for the second type of convergence criterion.

Alternatively or additionally, step S11 may interrupt the processing of the current signal segment y if a predefined time limit is exceeded, or if the convergence parameter value indicates a significant divergence between iterations. The time limit may e.g. be represented by a number of time steps or a number of iterations (of steps S3-S11). If the time limit is exceeded or divergence is detected, the method may be either aborted or proceed to step S12 for generation of output data or to step S1 for processing of another signal segment.

Figure 10A:
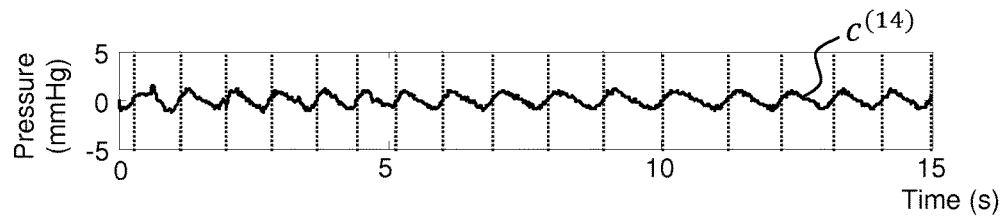
FIGS. 10(a)-10(b) are plots of filtered heart signals generated by the method in FIG. 7.
Figure 10B:
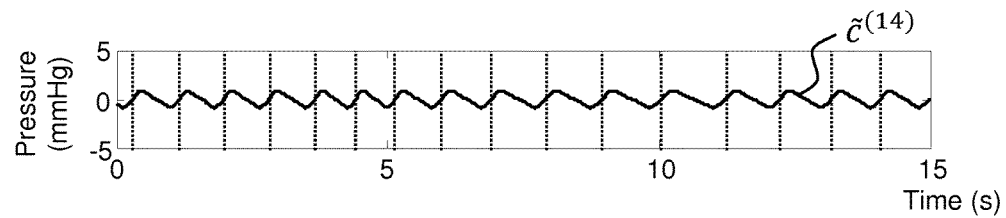
Figure 10C:
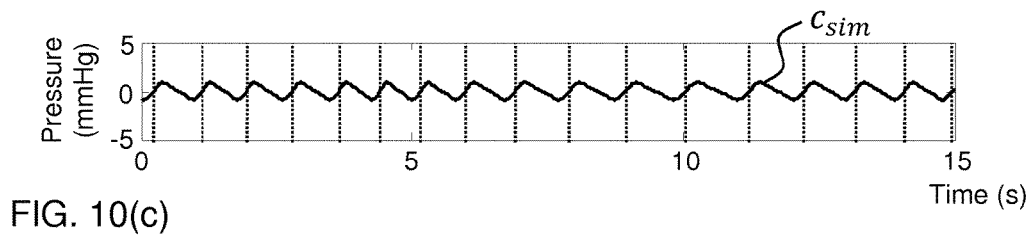
FIG. 10(c) is a plot of the actual heart signal that is embedded in the pressure signal processed by the method in FIG. 7.
Figure 10D:
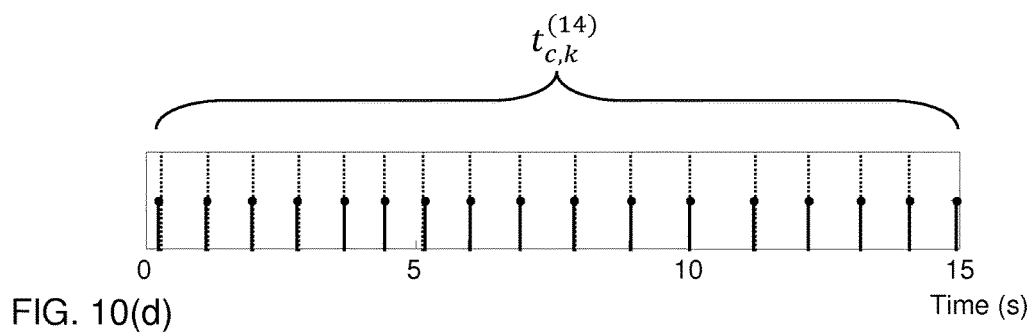
FIG. 10(d) is a plot comparing the timing of heart pulses in the filtered heart signals in FIGS. 10(a)-10(b) and the actual heart signal in FIG. 10(c).

To illustrate the effectiveness of the inventive filtering technique, FIG. 10(a) shows the filtered heart signal $c^{(14)}$ that is generated by step S3 (block 21) after 14 completed iterations of the method in FIG. 7, and FIG. 10(b) shows the corresponding heart template signal $\tilde{c}^{(14)}$ generated by step S6 (block 22). The vertical dotted lines in FIGS. 10(a)-10(b) indicate the reference times for the apparent heart cycles. The signals are generated based on a simulated pressure signal P, and FIG. 10(c) illustrates the simulated heart signal $c_{sim}$ that is embedded in the signal segment y that has been processed. As seen, there is a close resemblance between the heart template signal $\tilde{c}^{(14)}$ and the true signal $c_{sim}$. There is also proper correspondence between the filtered heart signal $c^{(14)}$ and the signal $c_{sim}$. FIG. 10(d) compares the estimated reference times for the apparent heart pulses in the signals $c^{(14)}$, $\tilde{c}^{(14)}$ (vertical dashed lines) and the actual references times for the heart pulses in the signal $c_{sim}$ (full lines with dot). As seen, the inventive technique is capable of accurately estimating the timing for each heart pulse. It should be realized that the inventive filtering technique operates to separate the heart pulses and the pump pulses, where the heart pulses are represented with proper timing, magnitude and shape in the heart template signal $\tilde{c}$ and the filtered heart signal c, and the pump pulses are represented in the pump template signal $\tilde{p}$ and the filtered pump signal p.

Step S12 may generate the output data in many different forms. The output data may represent either the heart pulses or the pump pulses in the signal segment y. In one embodiment, step S12 outputs a "heart signal", which is generated based on the signal $\tilde{c}$ (or the signal c) to represent the timing, magnitude and shape of heart pulses in the pressure signal P. If the signal segments y are non-overlapping in the pressure signal P, step S12 may form the heart signal by concatenating the signals $\tilde{c}$ (or c) that the separation process produces for consecutive signal segments y. If the signal segments y are partially overlapping in the pressure signal P, step S12 may generate the heart signal by combining (e.g. averaging) overlapping portions in the signals $\tilde{c}$ (or c) that are generated for consecutive signal segments. Combining overlapping portions will improve the quality of the heart signal, albeit at the cost of increased computational load. The heart signal may be further processed by step S12, or in a separate process, for detection of a disconnection of the venous access device 2" from the vascular access 3 based on a disappearance of heart pulses in the heart signal, as is well-known in the art, or for predicting rapid symptomatic blood pressure decrease, e.g. according to any one of the techniques disclosed in WO2011/080190, which is incorporated herein by reference. In another embodiment, step S12 outputs "heart timing data", e.g. in the form of the reference times [$t_c$] for the heart cycles or in the form of the heart cycle lengths. The heart timing data or the heart signal may be further processed by step S12, or a separate process, for computation of a parameter value that represents one of more of the heart rate variability (HRV), the heart rate (HR), the heart rate turbulence (HRT), the rate of ectopic beats (ectopic beat count, EBC), or the origin of ectopic beats (e.g. atria/ventricular), e.g. according to any one of the techniques disclosed in WO2011/080189, which is incorporated herein by reference. In another embodiment, step S12 outputs a "heart pulse profile", e.g. in the form of the heart cycle profile $\bar{c}$, or part thereof. The heart pulse profile or the heart signal may be further processed by step S12, or a separate process, for computation of a parameter value that represents the arterial status (arterial stiffness) of the blood vessels, the degree of calcification of the blood vessels, and the status of the vascular access, e.g. according to any one of the techniques disclosed in aforesaid WO2011/080189, or for detection of a reversed positioning of the access devices 2', 2" in the vascular access 3, e.g. according to any one of the techniques disclosed in WO2011/080188, which is incorporated herein by reference. The heart timing data, the heart pulse profile or the heart signal may be further processed by step S12, or a separate process, for estimation of the cardiac output or the blood flow rate through the vascular access ("access flow"), e.g. according to any one of the techniques disclosed in WO2011/080194, which is incorporated herein by reference. In another embodiment, step S12 outputs a "pump signal", which is generated based on the signal $\tilde{p}$ (or the signal p) to represent the shape, magnitude and timing of pump pulses in the pressure signal P. The pump signal may be further processed by step S12, or in a separate process, for detection of a disconnection of the venous access device 2" from the vascular access 3 based on a changes in the pump pulses, e.g. according to the techniques disclosed in WO2011/080187, which is incorporated herein by reference. In another embodiment, step S12 outputs "pump timing data", e.g. in the form of the reference times [$t_p$] for the pump cycles or in the form of the pump cycle lengths. The pump timing data or the pump signal may be further processed by step S12, or a separate process, for computation of the blood pumping rate of the pump, or to detect a fault condition in the pump 4. In another embodiment, step S12 outputs a "pump pulse profile", e.g. in the form of the pump cycle profile $\bar{p}$, or part thereof. The pump pulse profile, the pump timing data or the pump signal may be further processed by step S12, or a separate process, for detection of a fault condition in the pump 4, such as imbalanced rollers, lack of occlusion between rollers and tube segment etc, e.g. according to the techniques disclosed in aforesaid WO2011/080187.

Implementation Example

Below follows a brief mathematical description of an implementation of the principles described in the foregoing. The description is given with reference to the steps in FIG. 7.

Step S2

The speed of the blood pump is typically known beforehand since it is set for the dialysis machine by the clinical staff. However, to make the proposed method independent of the machine settings, the number of pump revolutions in a certain time interval, denoted by $N_p$, is determined from the zero crossings of the observed signal y(t), see FIG. 8(b). If the pump speed for some reason is altered by the staff during treatment, it is straightforward to re-estimate $N_p$. Initially, the pump speed is assumed to be constant with period length $T_p$, corresponding to one complete revolution of 360 degrees. The onset time of the k:th revolution is given by $$t_{p,k} = kT_p, k=0,,N_p-1. \quad (1)$$

For simplicity, the onset time of the first revolution is assumed to be at 0. An initial pump cycle profile $\bar{p}(t;T_p)$ is obtained by averaging all $N_p$ revolutions, using the assumption on periodicity in (1), $$\bar{p}(t; T_p) = \frac{1}{N_p} \sum_{k=0}^{N_p-1} y(t + kT_p), \quad 0 \le t < T_p. \quad (2)$$

The least squares error (LSE) criterion is employed to find that value of $T_p$ which provides the best fit of the periodic extension of $\bar{p}(t;T_p)$, i.e., $$\tilde{p}^{(0)}(t + kT_p) = \bar{p}(t;T_p), \quad 0 \le t < T_p, \quad (3)$$

to $y(t)$ over $N_p$ revolutions. An example of $\tilde{p}^{(0)}(t)$ is found in FIGS. 8(*a*)-8(*b*). The LSE is given by $$\varepsilon_p(T_p) = \frac{1}{N_p T_p} \int_0^{N_p T_p} (\tilde{p}(t; T_p) - y(t))^2 \, dt, \quad (4)$$

$$\hat{T}_p = \arg \min_{(1-\eta_p)\bar{T}_p < T_p < (1+\eta_p)\bar{T}_p} \varepsilon_p(T_p), \quad (5)$$

where minimization is performed over a search interval defined by the mean period length $\bar{T}_p$ (determined from $N_p$), the times of the zero crossings, and a search interval width defined by $\eta_p$ ($0 < \eta_p < 1$). It should be noted that the pump cycle profile in (2) is re-computed for all examined values of $T_p$ in the search interval. The superscript "(0)" indicates that the estimate is initial, subsequently to be replaced by the iteration index "(j)".

Step S3

Subtraction of the initial pump template signal, produced by periodical extension of the pump cycle profile in (3), from $y(t)$ produces an initial estimate of the heart signal, i.e. the filtered heart signal:

$$c^{(0)}(t) = y(t) - \tilde{p}^{(0)}(t). \quad (6)$$

Steps S4-S6

The number of heart cycles $N_c^{(0)}$ and related onset times $t_{c,k}^{(0)}$, $k = 0, N_c^{(0)}$ are determined from the zero crossing pattern of a low-pass filtered version of $c^{(0)}(t)$ in (6). Filtering reduces the influence of pump-related residuals, which may be seen as sharp valleys in the beginning of FIG. 8(*c*). It should be noted that $N_c$ is considerably more challenging to estimate than $N_N$ from the zero crossings, not only because the heart pulses are much smaller in amplitude than the pump pulses, but also that residuals of the pump pulses are present in $c^{(0)}(t)$. Therefore, the number of heart cycles $N_c$ is subject to iterative estimation.

The initial heart cycle profile $\bar{c}^{(0)}(t)$ is obtained by scaling each of the heart cycles in time with the factors $a_{c,k}^{(0)}$ so that their respective lengths are normalized prior to averaging, $$\bar{c}^{(0)}(t) = \frac{1}{N_c^{(0)}} \sum_{k=0}^{N_c^{(0)}-1} c^{(0)}(a_{c,k}^{(0)} t + t_{c,k}^{(0)}), \quad 0 \le t < \bar{T}_c^{(0)}, \quad (7)$$

where $$\bar{T}_c^{(0)} = \frac{t_{c,N_c^{(0)}}^{(0)} - t_{c,0}^{(0)}}{N_c^{(0)}}, \quad (8)$$

$$T_{c,k}^{(0)} = t_{c,k+1}^{(0)} - t_{c,k}^{(0)}, \quad (9)$$

$$a_{c,k}^{(0)} = \frac{T_{c,k}^{(0)}}{\bar{T}_c^{(0)}}, \quad (10)$$

for $k = 0, N_c^{(0)} - 1$.

The iterative estimation procedure begins by scaling the heart cycle profile $\bar{c}^{(j)}(t)$ with respect to the variable $T_{c,k}^{(j+1)}$, denoting the length of the k:th heart cycle, so that it best fits the filtered heart signal $c^{(j)}(t)$ in the LSE sense. In mathematical terms, the optimization is given by $$\hat{T}_{c,k}^{(j+1)} = \arg \min_{\eta_{c,0} \bar{T}_c^{(j)} < T_{c,k}^{(j+1)} < \eta_{c,1} \bar{T}_c^{(j)}} \varepsilon_c(T_{c,k}^{(j+1)}), \quad (11)$$

where $$\varepsilon_c(T_{c,k}^{(j+1)}) = \frac{1}{T_{c,k}^{(j+1)}} \int_0^{T_{c,k}^{(j+1)}} \left( c^{(j)}(t + \hat{t}_{c,k}^{(j+1)}) - \bar{c}^{(j)} \left( t \cdot \frac{\bar{T}_c^{(j)}}{T_{c,k}^{(j+1)}} \right) \right)^2 dt. \quad (12)$$

The lower and upper search limits $\eta_{c,0}$, and $\eta_{c,1}$ are chosen such that not only normal sinus rhythm may be detected, but also premature ventricular beats. Note that the optimization is performed sequentially, i.e., for one heart cycle at a time.

The onset time $t_{c,k}^{(j+1)}$ of the heart cycle $c^{(j)}(t)$ which is fitted to the time-scaled heart cycle profile in (12) is given by the sum of the lengths of the preceding heart cycles $$\hat{t}_{c,k}^{(j+1)} = \sum_{l=0}^{k-1} \hat{T}_{c,l}^{(j+1)}, \quad k = 1, , N_c^{(j+1)} - 1. \quad (13)$$

Updated versions of the heart cycle profile $\bar{c}^{(j+1)}(t)$ and the mean heart cycle length $\bar{T}_c^{(j+1)}$ are computed analogously to (7) and (10), respectively. From knowledge of $\bar{c}^{(j+1)}(t)$ and $\hat{t}_{c,k}^{(j+1)}$, the heart template signal $\tilde{c}^{(j+1)}(t)$, is updated through concatenation until the entire observation interval is covered, see FIG. 8(*c*), $$\tilde{c}^{(j+1)}(\hat{a}_{c,k}^{(j+1)} t + \hat{t}_{c,k}^{(j+1)}) = \bar{c}^{(j+1)}(t), \quad 0 \le t < \bar{T}_c, \quad (14)$$

for $k = 0, N_c^{(j+1)} - 1$. The number of heart cycles $N_c^{(j+1)}$ is updated for each iteration by finding the maximum number of heart cycles that fits within the observed signal segment $y(t)$.

Step S7

The filtered pump signal is updated by subtracting the heart template signal from the observed signal segment, $$p^{(j+1)}(t) = y(t) - \tilde{c}^{(j+1)}(t) \quad (15)$$

Steps S8-S10

The initial assumption in (1) of a constant period length T is now relaxed so that each pump revolution has its own individual period length $T_{p,k}$, thereby accounting for the fact that pump speed may vary slightly from revolution to revolution. Hence, the above optimization in (11) for iterative estimation of cardiac information is also employed for finding $T_{p,k}$, except that the search interval is given by that in (5).

Although the error $\varepsilon_p$ may be defined in analogy with the error $\varepsilon_c$ in (12), the present Implementation Example calculates the error $\varepsilon_p$ by replacing the integrand in (12) for its second derivative. This is done to de-emphasize rapid changes in the heart template signal $\tilde{c}$. Another difference is that the error $\varepsilon_p$ is minimized for half revolutions (180°), instead of full revolutions, to potentially achieve a better fit to the signal segment y. These two differences have been found to decrease the number of iterations needed as well as to reduce the transient residuals of pump pulses in the heart template signal $\tilde{c}$.

Although the updated pump cycle profile $\bar{p}^{(j+1)}(t)$ may be generated by averaging pump cycles (given by $T_{p,k}$) in the filtered pump signal $p^{(j+1)}(t)$, the present Implementation Example instead generates $\bar{p}^{(j+1)}(t)$ by averaging corresponding pump cycles in the signal segment y(t), where the corresponding pump cycles in the signal segment y(t) are likewise given by $T_{p,k}$. Thus, the pump cycles identified in $p^{(j+1)}(t)$ are mapped to corresponding pump cycles in y(t), which are used for calculating the pump cycle profile $\bar{p}^{(j+1)}(t)$. This has been found to improve stability, by reducing the risk that residuals of the heart pulses gradually migrate into the pump template signal $\tilde{p}^{(j+1)}(t)$ as the iterative procedure progresses.

The pump cycle profile is updated by scaling each of the pump cycle profiles in time with the factor $a_{p,k}^{(j+1)}$ so that their lengths are normalized prior to averaging, $$\bar{p}^{(j+1)}(t) = \frac{1}{N_p} \sum_{k=0}^{N_p-1} y(a_{p,k}^{(j+1)} t + t_{p,k}^{(j+1)}), \ 0 \le t < \hat{T}_p, \quad (16)$$

where the scaling factors $a_{p,k}^{(j+1)}$ are defined in analogy with (10).

Analogous to the heart template signal, the pump template signal $\tilde{p}^{(j+1)}(t)$ is generated through concatenation so that the entire observation interval is covered, $$\tilde{p}^{(j+1)}(a_{p,k}^{(j+1)} t + \hat{t}_{p,k}^{(j+1)}) = \bar{p}^{(j+1)}(t), \ 0 \le t < \hat{T}_p, \quad (17)$$

for k=0,,$N_c^{(j+1)}$−1.

Step S11

The alternating, iterative estimation procedure is considered to have converged when the following criterion is fulfilled:

$$\max_k \left| \hat{t}_{p,k}^{(j+1)} - \hat{t}_{p,k}^{(j)} \right| < \delta, \quad (18)$$

where $\delta$ denotes the convergence tolerance. As long as the criterion in (18) remains unfulfilled, the iteration index j is incremented by 1 and the procedure returns to step S3 which updates the filtered heart signal by subtracting the pump template signal from the observed signal segment, $$c^{(j+1)}(t) = y(t) - \tilde{p}^{(j+1)}(t) \quad (19)$$

If convergence is not reached within L iterations, the procedure is terminated. It may be preferable to test convergence on the pump onset times $\hat{t}_{p,k}$ which may be more reliable than the cardiac onset times $\hat{t}_{c,k}$ since the pump pulses dominate over the heart pulses, and the number of pump cycles remains fixed during the estimation procedure.

The method according to the Implementation Example has been operated on individual signal segments within a time window of 1 minute in the pressure signal to evaluate the performance, as presented below.

Figure 11:
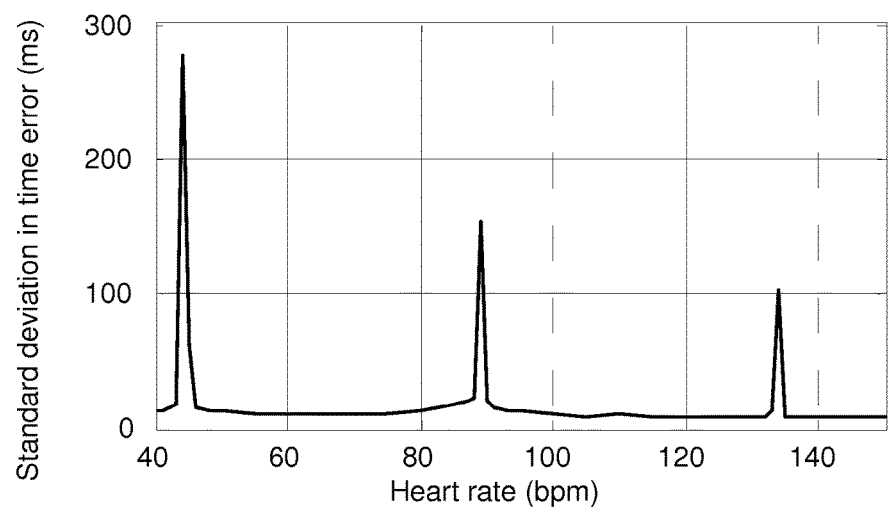
FIGS. 11-12 are plots illustrating errors in timing estimates of heart cycles in a pressure signal for different properties of the heart cycles.

The performance of the method was validated at heart rates ranging from 40 to 150 bpm. This range is considered covering the heart rates of most dialysis patients. The relative heart amplitude was 12%. The average standard deviation between the simulated and estimated heartbeat onset times (time error) for 100 signal segments is plotted in FIG. 11. The simulated blood flow was 400 ml/min per minute which corresponds to a pump rate with harmonics of 44, 89, and 134 rpm. It is seen that the performance is less accurate when the heart rate is overlapping any harmonic frequency of the pump. In these cases, the method is less suitable for separating the heart pulses from the pump pulses.

Figure 12:
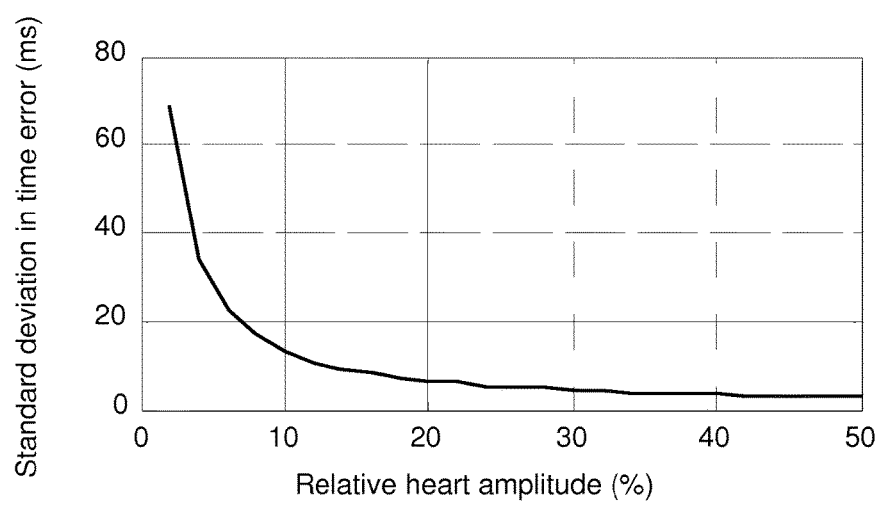

The performance was also studied for different heart amplitudes. Pressure signals with a heart pulse amplitude between 2% and 50% relative to the pump pulse amplitude were simulated. The heart rate was 67 bpm. For each amplitude 100 signal segments were analyzed. The average standard deviation of the difference between the estimated and simulated heart pulse occurrence times (time error) was calculated, see FIG. 12. When the heart amplitude is low, noise dominates and disturbs the estimated onset times.

Figure 13:
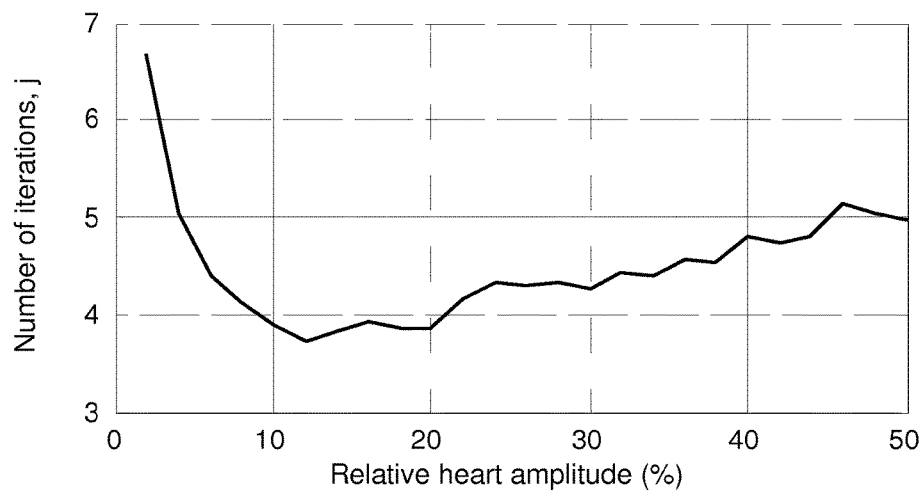
FIG. 13 is a plot illustrating convergence rate as a function of the relative magnitude of the heart pulses in the pressure signal.

The number of iterations required to reach convergence is plotted in FIG. 13. The number of iterations needed increases with increasing relative magnitude of the heart pulses. One reason may be that the initial pump signal estimate ($\tilde{p}^{(0)}$) becomes less accurate with increasing relative magnitude of the heart pulses. For weak heart pulses, the number of iterations is increased due to increased influence of noise.

Figure 14:
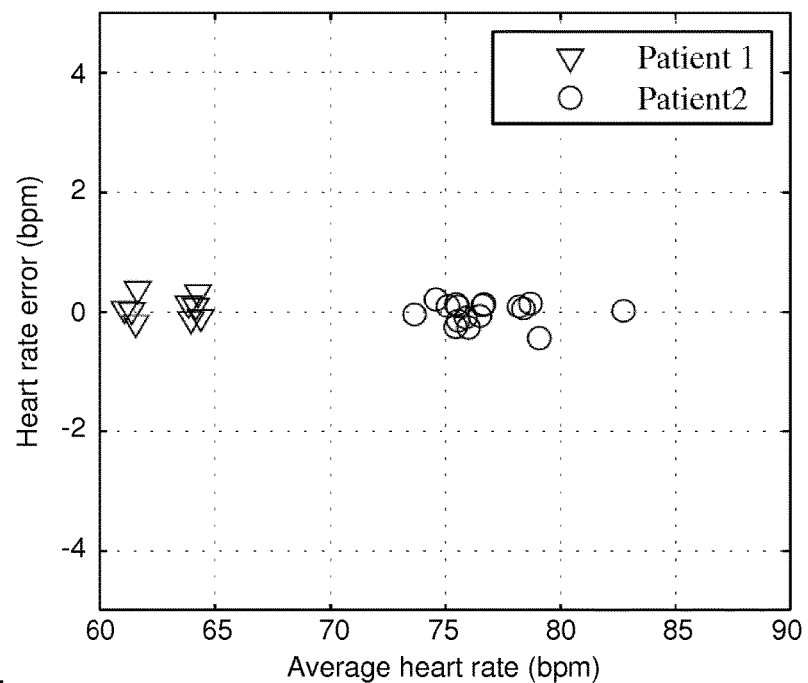
FIG. 14 is a plot of experimental data showing error in estimated heart rate as a function of average heart rate.

The method according to the Implementation Example was also applied to pressure recordings from two subjects. The average heart rate for signal segments was calculated using the estimated onset times. The heart rate was also calculated based on a reference PPG signal from a photoplethysmography (PPG) sensor attached to the subject. Onset times were calculated from the reference PPG signal as occurring at the half rise time of each heart beat. A comparison between the heart rates is seen in FIG. 14. The results show an excellent agreement between heart rate estimated from extracorporeal venous pressure signal and the reference PPG signal for the two subjects. The error is well within one beat per minute.

Irrespective of representation, the filtering device 7 may be implemented by special-purpose software (or firmware) run on one or more general-purpose or special-purpose computing devices. In this context, it is to be understood that each of the blocks in FIGS. 5-6 may refer to a conceptual equivalent of a method step (i.e. a means for performing a dedicated function); there is not always a one-to-one correspondence between the blocks and particular pieces of hardware or software routines. For example, a processing unit may serve as one block when executing one set of instructions, but serve as another block when executing another set of instructions. Such a software controlled computing device may include one or more processing units (cf. 9a in FIG. 1), e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The device 7 may further include a system memory and a system bus that couples various system components including the system memory (cf. 9b in FIG. 1) to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The device 7 may include one or more communication interfaces, such as a serial interface, a parallel interface, a USB interface, a wireless interface, a network adapter, etc, as well as one or more data acquisition devices, such as an A/D converter. The special-purpose software may be provided to the device 7 on any suitable computer-readable medium, including a record medium or a read-only memory.

It is also conceivable that some (or all) blocks are fully or partially implemented by dedicated hardware, such as an FPGA, an ASIC, or an assembly of discrete electronic components (resistors, capacitors, operational amplifier, transistors, filters, etc), as is well-known in the art.

It should be emphasized that the invention is not limited to digital signal processing, but could be fully implemented by a combination of analog devices.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

In all of the foregoing examples, the respective template signal (heart template signal $\tilde{c}$, pump template signal 13) is first estimated (in steps S4-S6, S8-S10) and then subtracted (in steps S7, S3) from the signal segment y to produce a difference signal (filtered pump signal p, filtered heart signal c). The signal segment y may be represented as a first vector, the respective template signal $\tilde{c}$, $\tilde{p}$ may be represented as a second vector, and the difference signal p, c may be generated as a third vector by element-wise subtraction of the second vector from the first vector. In an equivalent implementation, the third vector is generated by sequentially generating an element in the second vector (template signal $\tilde{c}$, $\tilde{p}$) and subtracting this element from the corresponding element in the first vector (signal segment y). In essence, this corresponds to subtracting the second vector from the first vector.

As indicated above, it is also conceivable to start the iterative processing of the signal segment y based on an initial template signal for the heart pulses. The skilled person is readily able to modify the block diagram in FIG. 5 and the flow chart in FIG. 7 accordingly. Thus, all embodiments, variants, examples and implementations of the iterative processing based on an initial template signal for the pump pulses, as described herein, are equally applicable, by analogy, to the iterative processing based on an initial template signal for the heart pulses. Taking FIG. 5 as an example, block 24A may be modified to supply a initial template signal $\tilde{c}^{(0)}$ for the heart pulses to block 21, block 22 may be modified to acquire and process a filtered pump signal p from block 21 so as to generate a template signal $\tilde{p}$ for the pump pulses, and block 24 may be modified to acquire and process a filtered heart signal c from block 23 so as to generate a template signal $\tilde{c}$ for the heart pulses. Block 24A may generate the initial template signal $\tilde{c}^{(0)}$ based on a reference signal (corresponding to REF in FIG. 5) that indicates the rate or timing of the heart pulses. The reference signal may be acquired from any conventional pulse sensor attached to the subject, such as a pulse watch, a photoplethysmograph (PPG) such as a pulse oximeter, an electrocardiograph (ECG), etc. In another example, the reference signal is a pressure signal generated by another pressure sensor in the EC circuit (e.g. the sensor 6a in FIG. 1) which is arranged to detect pressure waves originating from the heart. It is conceivable that block 24A estimates not only the timing, but also the shape and magnitude of the heart cycles based on the reference signal.

The inventive technique is applicable in all types of EC circuits in which blood is taken from the systemic blood circuit of a subject to have a process applied to it before it is returned to the subject. Such extracorporeal blood circuits include circuits for hemodialysis, hemofiltration, hemodiafiltration, plasmapheresis, apheresis, extracorporeal membrane oxygenation, assisted blood circulation, and extracorporeal liver support/dialysis. The inventive technique is likewise applicable for pulse separation in other types of extracorporeal blood circuits, such as circuits for blood transfusion, as well as heart-lung-machines. The inventive technique is also applicable to EC circuits that contain other liquids than blood and are connected to the cardiovascular system of a human or animal subject, including systems for intravenous therapy, infusion pumps, automated peritoneal dialysis (APD) systems, etc. Examples of such liquids include medical solutions, dialysis fluids, infusion liquids, water, etc.

The inventive technique is generally applicable to separate a repetitive sequence of physiological pulses from a repetitive sequence of interference pulses in a pressure signal which is acquired from a pressure sensor in an EC circuit connected to a human or animal subject. The physiological pulses may originate from any repetitive (periodic) physiological pulse generator in the subject, including the heart, the breathing system, the autonomous system for blood pressure regulation and the autonomous system for body temperature regulation. The interference pulses may originate from any interference generator that is located in or is associated with the EC circuit to produce repetitive interference pulses in the pressure signal. In this context, "associated with" implies that the interference generator need not be included in the EC circuit but is capable of generating pressure waves that propagate in the EC circuit to the pressure sensor.

If the pressure signal P contains physiological pulses from more than one pulse generator in the subject, the input block 18 in FIG. 5 may be configured to apply a low-pass, band-pass or high-pass filter, or any combination thereof, so as to selectively transmit a limited frequency range associated with the physiological pulses to be separated from the interference pulses in the pressure signal P. The limited frequency range may e.g. be set to approx. 0.5-3 Hz if the physiological pulses originate from the heart, approx. 0.15-0.4 Hz if the physiological pulses originate from the breathing system, approx. 0.04-0.14 Hz if the physiological pulses originate from the autonomous systems for blood pressure regulation, and approx. 0.001-0.1 Hz if the physiological pulses originate from autonomous system for temperature regulation.

The interference generator may be any type of pumping device, not only rotary peristaltic pumps as disclosed above, but also other types of positive displacement pumps, such as linear peristaltic pumps and diaphragm pumps. Further, the interference generator may be one or more valves or flow restrictors that are installed in or associated with the fluid containing system. The valves and flow restrictors may be operable to periodically stop a flow of fluid, change a flow rate of fluid, or change a fluid flow path. The valves and flow restrictors may also be included in a system for degassing of a fluid or a system for changing the static pressure of a fluid. In another example, the interference generator is a balancing chamber as used in certain types of dialysis systems.

The techniques described herein may be extended for separation of pulses with more than two different origins.

Figure 15:
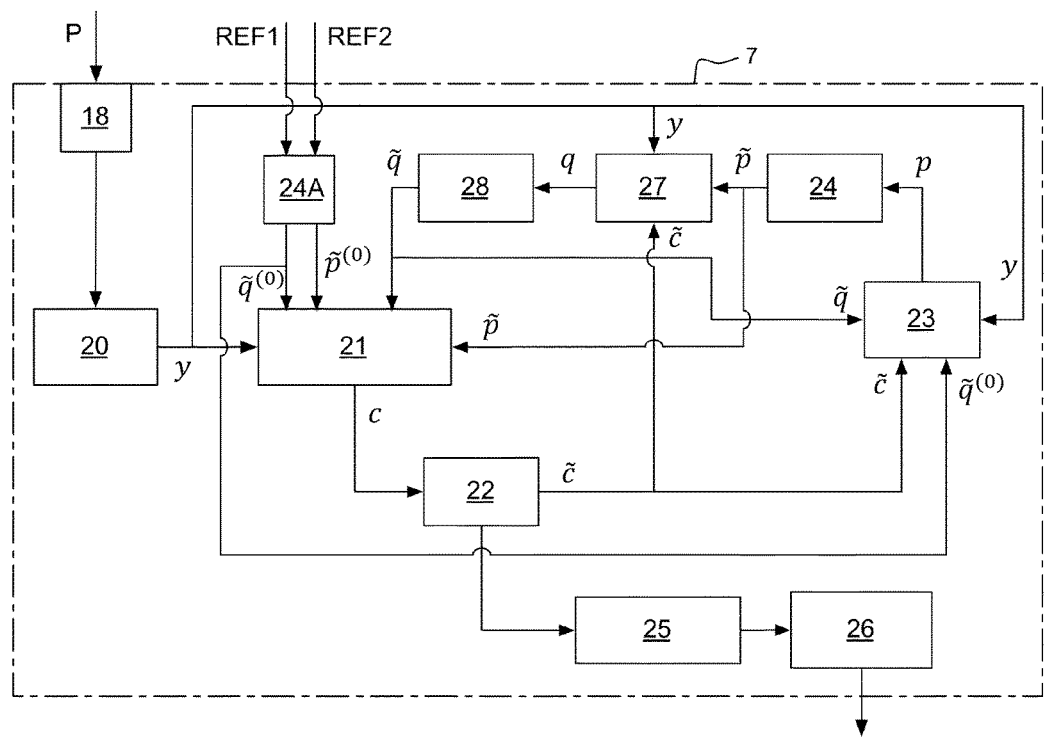
FIG. 15 is a block diagram of a filtering device according to another embodiment.

FIG. 15 is merely given as an example of a block diagram for a device 7 which corresponds to the device 7 in FIG. 5 but is implemented for separating pulses from three different pulse generators. For this purpose, the device 7 includes an additional subtraction block 27 and an additional refinement block 28, which may configured in correspondence with subtraction blocks 21, 23 and refinement blocks 22, 24. Furthermore, the initiation block 24A is configured to generate initial template signals for two different types of pulses. In the illustrated example, the device 7 is configured to separate heart pulses, pump pulses and a third type of pulses, denoted auxiliary pulses, which may originate either from a further physiological pulse generator in the subject or a further interference generator associated with the EC circuit. In the illustrated example, the initiation block 24A generates an initial template signal $\tilde{p}^{(0)}$ for the pump pulses and an initial template signal $\tilde{q}^{(0)}$ for the auxiliary pulses, e.g. based on one reference signal REF1 for the pump 4 and one reference signal REF2 for the origin of the auxiliary pulses. As seen, the device 7 generates a filtered heart signal c, a heart template signal $\tilde{c}$, a filtered pump signal p, a pump template signal $\tilde{p}$, a filtered signal q for the auxiliary pulses, and a template signal $\tilde{q}$ for the auxiliary pulses. The structure and operation of the device 7 in FIG. 15 should be apparent from foregoing detailed description and will not be described in further detail.

The pressure sensor may be of any type, e.g. operating by resistive, capacitive, inductive, magnetic, acoustic or optical sensing, and using one or more diaphragms, bellows, Bourdon tubes, piezo-electrical components, semiconductor components, strain gauges, resonant wires, accelerometers, etc.

The inventive technique need not operate on real-time data, but could be used for processing off-line data, such as a previously recorded pressure signal.

The invention claimed is:

1. A device for processing a pressure signal obtained from a pressure sensor in an extracorporeal fluid circuit, said device comprising:
   an input for receiving the pressure signal from the pressure sensor; and
   a signal processor connected to the input and being configured to:
      extract, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit;
      process the signal segment for separation of the interference pulses from the physiological pulses by:
         a) subtracting at least one initial template signal from the signal segment to generate a first difference signal that represents the sequence of physiological pulses and residuals of the interference pulses;
         b) processing the first difference signal to generate a first template signal in which the residuals of the interference pulses are suppressed in relation to the sequence of physiological pulses;
         c) subtracting at least the first template signal from the signal segment to generate a second difference signal that represents the sequence of interference pulses and residuals of the physiological pulses; and
         d) processing the second difference signal to generate a second template signal in which the residuals of the physiological pulses are suppressed in relation to the sequence of interference pulses; and
      evaluating a property of the extracorporeal fluid circuit using the second template signal.

2. The device of claim 1, wherein the signal processor is configured to, subsequent to the steps a)-d), process the signal segment for separation of the interference pulses from the physiological pulses by:
   e) subtracting at least the second template signal from the signal segment to generate the first difference signal; and
   repeating the steps b)-e) in at least one iteration.

3. The device of claim 2, wherein the signal processor is configured to repeatedly execute steps b)-e) until a predefined convergence criterion is fulfilled or until a predefined time limit is exceeded.

4. The device of claim 3, wherein the predefined convergence criterion is defined to detect a predefined suppression of the residuals of the physiological pulses in the second difference signal or the second template signal, or to detect a predefined suppression of the residuals of the interference pulses in the first difference signal or the first template signal.

5. The device of claim 1, wherein the signal processor is further configured, in step b), to: identify a set of predefined first cycles of the physiological pulses in the first difference signal, determine a first signal profile for each of the predefined first cycles, and generate the first template signal by tiling the first signal profiles such that the timing of the first signal profiles in the first template signal matches the timing of the set of predefined first cycles in the first difference signal.

6. The device of claim 5, wherein the signal processor is further configured, in step b), to: identify a respective reference time point for each of the predefined first cycles in the first difference signal, and generate the first template signal by tiling and time-scaling the first signal profiles with respect the reference time points.

7. The device of claim 5, wherein the signal processor is further configured, in step b), to: determine a length of the respective predefined first cycle in the first difference signal; and select the first signal profile among at least two candidate profiles based on the length of the respective predefined first cycle.

8. The device of claim 5, wherein the signal processor is further configured, in step b), to determine the first signal profile by at least one of:
   retrieving the first signal profile from an electronic memory associated with the device, wherein the first signal profile is fixed and pre-defined, or generated and stored in the electronic memory by the signal processor during processing of a preceding signal segment in the pressure signal;
   generating the first signal profile as a function of the predefined first cycles in the first difference signal;
   generating the first signal profile by processing the pressure signal while the interference generator is intermittently disabled; and
   generating the first signal profile by processing a further pressure signal acquired from a further pressure sensor in the extracorporeal fluid circuit.

9. The device of claim 1, wherein the signal processor is further configured, in step d), to: identify a set of predefined second cycles in the second difference signal; determine a second signal profile for each of the predefined second cycles; and generate the second template signal by tiling the second signal profiles such that the timing of the second signal profiles in the second template signal matches the timing of the set of predefined second cycles in the second difference signal.

10. The device of claim 9, wherein the signal processor is further configured, in step d), to: identify a respective reference time point for each of the predefined second cycles in the second difference signal, and generate the second template signal by tiling and time-scaling the second signal profiles with respect to the reference time points.

11. The device of claim 9, wherein the signal processor is further configured, in step d), to determine the second signal profile by one of:
    retrieving the second signal profile from an electronic memory associated with the device, wherein the second signal profile is fixed and pre-defined, or generated and stored in the electronic memory by the signal processor during processing of a preceding signal segment in the pressure signal;
    retrieving the second signal profile from the electronic memory based on an operating condition of the extracorporeal fluid circuit, wherein a plurality of second signal profiles are stored in the electronic memory in association with different operating conditions;
    generating the second signal profile as a function of the predefined second cycles in the second difference signal;
    mapping the predefined second cycles in the second difference signal to corresponding subsets of the signal segment, and generating the second signal profile as a function of the corresponding subsets; and
    generating the second signal profile by processing a further pressure signal acquired from a further pressure sensor in the extracorporeal fluid circuit.

12. The device of claim 1, wherein the signal processor is further configured, in step d), to: determine a current operating condition of the interference generator; and generate the second template signal as a combination of sinusoids at a plurality of harmonic frequencies associated with the current operating condition.

13. The device of claim 1, wherein the signal processor is further configured, in step a), to: acquire said at least one initial template signal as an initial estimate of the shape, the magnitude and the timing of the interference pulses in the signal segment.

14. The device of claim 1, wherein the signal processor is further configured, in step a), to acquire said at least one initial template signal by one of:
    determining a current operating condition of the interference generator, determining an initial signal profile for predefined second cycles in the signal segment, and generating said at least one initial template signal by tiling the initial signal profiles such that the timing of the initial signal profiles in said at least one initial template signal corresponds to the current operating condition;
    determining a current operating condition of the interference generator, and generating said at least one initial template signal as a combination of sinusoids at a plurality of harmonic frequencies associated with the current operating condition; and
    retrieving said at least one initial template signal from an electronic memory associated with the device, wherein said at least one initial template signal is generated and stored in the electronic memory by the signal processor during processing of a preceding signal segment in the pressure signal, preferably as a function of at least one of the second difference signal, the second template signal, and the second signal profile generated during the processing of the preceding signal segment.

15. The device of claim 12, wherein the signal processor is further configured to determine the current operating condition of the interference generator by processing one of the signal segment, the first difference signal, the second difference signal, or a reference signal that represents the operation of the interference generator.

16. The device of claim 5, wherein each predefined first cycle is predefined to comprise a given number of physiological pulses.

17. The device of claim 9, wherein each predefined second cycle is predefined to comprise a given number of interference pulses.

18. The device of claim 9, wherein the interference generator includes a peristaltic pump comprising a rotor with at least one roller, and wherein each predefined second cycle pulse is predefined to correspond to a full revolution of the rotor.

19. The device of claim 1, wherein the signal processor is configured to extract the signal segment such that the signal segment comprises at least 2, and preferably at least 10, physiological pulses, and at least 2, and preferably at least 10, interference pulses.

20. A method of processing a pressure signal obtained from a pressure sensor in an extracorporeal fluid circuit, said method comprising:
    extracting, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit;
    subtracting at least one initial template signal from the signal segment to generate a first difference signal that represents the sequence of physiological pulses and residuals of the interference pulses;
    processing the first difference signal to generate a first template signal in which the residuals of the interference pulses are suppressed in relation to the sequence of physiological pulses;
    subtracting at least the first template signal from the signal segment to generate a second difference signal that represents the sequence of interference pulses and residuals of the physiological pulses;
    processing the second difference signal to generate a second template signal in which the residuals of the physiological pulses are suppressed in relation to the sequence of interference pulses; and
    evaluating a property of the extracorporeal fluid circuit using the second template signal.

21. A non-transitory computer-readable medium comprising computer instructions which, when executed by a processor, cause the processor to perform the method of claim 20.

22. A device for processing a pressure signal obtained from a pressure sensor in an extracorporeal fluid circuit, said device comprising:
    segmentation means configured to receive the pressure signal and extract, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit;

first subtraction means configured to subtract at least one initial template signal from the signal segment to generate a first difference signal that represents the sequence of physiological pulses and residuals of the interference pulses;

first refinement means configured to process the first difference signal to generate a first template signal in which the residuals of the interference pulses are suppressed in relation to the sequence of physiological pulses;

second subtraction means configured to subtract at least the first template signal from the signal segment to generate a second difference signal that represents the sequence of interference pulses and residuals of the physiological pulses;

second refinement means configured to process the second difference signal to generate a second template signal in which the residuals of the physiological pulses are suppressed in relation to the sequence of interference pulses; and evaluation means configured to evaluate a property of the extracorporeal fluid circuit using the second template signal.

23. A device for processing a pressure signal obtained from a pressure sensor in an extracorporeal fluid circuit, said device comprising:

an input for receiving the pressure signal from the pressure sensor; and a signal processor connected to the input and being configured to:

extract, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit;

process the signal segment for separation of the interference pulses from the physiological pulses by:

a) subtracting at least one initial template signal from the signal segment to generate a first difference signal that represents the sequence of interference pulses and residuals of the physiological pulses, b) processing the first difference signal to generate a first template signal in which the residuals of the physiological pulses are suppressed in relation to the sequence of interference pulses, c) subtracting at least the first template signal from the signal segment to generate a second difference signal that represents the sequence of physiological pulses and residuals of the interference pulses, and d) processing the second difference signal to generate a second template signal in which the residuals of the interference pulses are suppressed in relation to the sequence of physiological pulses; and evaluate a cardiovascular property of the subject using the second template signal.

24. A method of processing a pressure signal obtained from a pressure sensor in an extracorporeal fluid circuit, said method comprising:

extracting, from the pressure signal, a signal segment that comprises a sequence of interference pulses originating from an interference generator associated with the extracorporeal fluid circuit, and a sequence of physiological pulses originating from a physiological pulse generator in a subject which is connected to the extracorporeal fluid circuit;

subtracting at least one initial template signal from the signal segment to generate a first difference signal that represents the sequence of interference pulses and residuals of the physiological pulses;

processing the first difference signal to generate a first template signal in which the residuals of the physiological pulses are suppressed in relation to the sequence of interference pulses;

subtracting at least the first template signal from the signal segment to generate a second difference signal that represents the sequence of physiological pulses and residuals of the interference pulses;

processing the second difference signal to generate a second template signal in which the residuals of the interference pulses are suppressed in relation to the sequence of physiological pulses; and evaluating a cardiovascular property of the subject using the second template signal.

25. A non-transitory computer-readable medium comprising computer instructions which, when executed by a processor, cause the processor to perform the method of claim 24.

26. A device for processing a pressure signal obtained from a pressure sensor in an extracorporeal fluid circuit, said device comprising:

segmentation means configured to receive the pressure signal and extract, from the pressure signal, a signal segment that comprises a sequence of interference pulses originating from an interference generator associated with the extracorporeal fluid circuit and a sequence of physiological pulses originating from a physiological pulse generator in a subject which is connected to the extracorporeal fluid circuit;

first subtraction means configured to subtract at least one initial template signal from the signal segment to generate a first difference signal that represents the sequence of interference pulses and residuals of the physiological pulses;

first refinement means configured to process the first difference signal to generate a first template signal in which the residuals of the physiological pulses are suppressed in relation to the sequence of interference pulses;

second subtraction means configured to subtract at least the first template signal from the signal segment to generate a second difference signal that represents the sequence of physiological pulses and residuals of the interference pulses;

second refinement means configured to process the second difference signal to generate a second template signal in which the residuals of the interference pulses are suppressed in relation to the sequence of physiological pulses; and evaluation means configured to evaluate a cardiovascular property of the subject using the second template signal.

27. The device of claim 1, which is further configured to process a reference signal obtained from a reference sensor associated with the interference generator, and wherein the signal processor is configured to use information from the reference signal to separate the interference pulses from the physiological pulses.

28. The method of claim 20, which further includes processing a reference signal obtained from a reference sensor associated with the interference generator, and using information from the reference signal to separate the interference pulses from the physiological pulses.

29. The device of claim 22, which is further configured to process a reference signal obtained from a reference sensor associated with the interference generator, and use information from the reference signal to separate the interference pulses from the physiological pulses.

30. The device of claim 23, which is further configured to process a reference signal obtained from a reference sensor associated with the interference generator, and wherein the signal processor is configured to use information from the reference signal to separate the interference pulses from the physiological pulses.

31. The method of claim 24, which further includes processing a reference signal obtained from a reference sensor associated with the interference generator, and using information from the reference signal to separate the interference pulses from the physiological pulses.

32. The device of claim 26, which is further configured to process a reference signal obtained from a reference sensor associated with the interference generator, and use information from the reference signal to separate the interference pulses from the physiological pulses.

* * * * *